United States Patent
Greene

(10) Patent No.: US 9,656,017 B2
(45) Date of Patent: May 23, 2017

(54) INFUSION DELIVERY DEVICES AND METHODS

(71) Applicant: Howard E. Greene, Frankfort, MI (US)

(72) Inventor: Howard E. Greene, Frankfort, MI (US)

( * ) Notice: Subject to any disclaimer, the term of this patent is extended or adjusted under 35 U.S.C. 154(b) by 0 days.

(21) Appl. No.: 14/745,368

(22) Filed: Jun. 19, 2015

(65) Prior Publication Data

US 2015/0366945 A1    Dec. 24, 2015

Related U.S. Application Data

(60) Provisional application No. 62/015,073, filed on Jun. 20, 2014.

(51) Int. Cl.
| | |
|---|---|
| *G01N 33/48* | (2006.01) |
| *G01N 31/00* | (2006.01) |
| *G06G 7/48* | (2006.01) |
| *G06G 7/58* | (2006.01) |
| *A61M 5/142* | (2006.01) |
| *A61K 38/28* | (2006.01) |
| *A61M 5/14* | (2006.01) |

(52) U.S. Cl.
CPC ......... *A61M 5/14244* (2013.01); *A61K 38/28* (2013.01); *A61M 5/1407* (2013.01); *A61M 2005/14208* (2013.01); *A61M 2205/3584* (2013.01); *A61M 2205/50* (2013.01); *A61M 2205/505* (2013.01)

(58) Field of Classification Search
None
See application file for complete search history.

(56) References Cited

U.S. PATENT DOCUMENTS

| | | |
|---|---|---|
| 3,528,960 A | 9/1970 | Haas |
| 5,124,314 A | 6/1992 | Cooper |
| 5,514,646 A | 5/1996 | Chance et al. |
| 5,618,913 A | 4/1997 | Brange et al. |
| 5,686,411 A | 11/1997 | Gaeta et al. |

(Continued)

FOREIGN PATENT DOCUMENTS

| | | |
|---|---|---|
| EP | 0280534 B1 | 4/1993 |
| EP | 0254516 B1 | 1/1994 |

(Continued)

OTHER PUBLICATIONS

Huffman et al., Continuous Subcutaneous Pramlintide Infusion Therapy in Patients with Type 1 Diabetes: Observations from a Pilot Study, Endocr. Pract., 2009, 689-695, 15(7).

(Continued)

*Primary Examiner* — Larry D Riggs, II
(74) *Attorney, Agent, or Firm* — Acuity Law Group, P.C.; Daniel M. Chambers

(57) ABSTRACT

Devices that include multi-reservoir infusion devices and systems for dispensing compositions for the treatment of subjects with an amylin agonist (e.g., the amylin agonist analog, pramlintide), wherein amylin agonists are administered in certain differential bolus and basal ratios to an administered insulin, as well as methods, compositions, and kits and articles of manufacture comprising said compositions for use in the treatment of responsive patients with an amylin and an insulin in ratios thereof that are distinct for bolus and basal administration.

19 Claims, 9 Drawing Sheets

(56) References Cited

U.S. PATENT DOCUMENTS

| | | | |
|---|---|---|---|
| 5,700,662 A | 12/1997 | Chance et al. | |
| 5,750,497 A | 5/1998 | Havelund et al. | |
| 6,011,007 A | 1/2000 | Havelund et al. | |
| 6,114,304 A | 9/2000 | Kolterman et al. | |
| 6,136,784 A | 10/2000 | L'Italien et al. | |
| 6,251,856 B1 | 6/2001 | Markussen et al. | |
| 6,410,511 B2 | 6/2002 | L'Italien et al. | |
| 8,486,890 B2 | 7/2013 | Hansen et al. | |
| 2009/0018053 A1 | 1/2009 | L'Italien et al. | |
| 2010/0145303 A1* | 6/2010 | Yodfat | A61M 5/1408 604/506 |
| 2012/0191061 A1 | 7/2012 | Yodfat et al. | |
| 2013/0055816 A1 | 3/2013 | Masson et al. | |
| 2013/0245545 A1* | 9/2013 | Arnold | A61M 5/1723 604/66 |

FOREIGN PATENT DOCUMENTS

| | | |
|---|---|---|
| EP | 0214826 B1 | 10/1994 |
| EP | 0289287 B1 | 1/1998 |
| EP | 2036923 A1 | 3/2009 |
| WO | 96/15804 A1 | 5/1996 |
| WO | 03/053339 A2 | 7/2003 |
| WO | 2004/037168 A2 | 5/2004 |
| WO | 2007/104789 A2 | 9/2007 |
| WO | 2010028257 A1 | 3/2010 |
| WO | 2011031351 A1 | 3/2011 |
| WO | WO 2011/031351 * 3/2011 ............... A61B 5/00 | |

OTHER PUBLICATIONS

Micheletto et al., In Silico Design of Optimal Ratio for Co-Administration of Pramlintide and Insulin in Type 1 Diabetes, Diabetes Technol. Ther., 2013, 802, 806, 15(10).

Ryan et al., Pramlintide in the treatment of type 1 and type 2 diabetes mellitus, Clin. Ther., 2005, 1500-1512, 27(10).

Thabit et al., Closed-loop Insulin Delivery in Type 1 Diabetes, Endocrinol. Metab. Clin. North Am., 2012, 105-117, 41 (1).

Yan et al., Design of a mimic of nonamyloidogenic and bioactive human islet amyloid polypeptide (IAPP) as nanomolar affinity inhibitor of IAPP cytotoxic fibrillogenesis, Proc. Natl. Acad. Sci. U.S.A., 2006, 2046-2051, 103(7).

* cited by examiner

INFUSION DELIVERY DEVICES AND METHODS

RELATED APPLICATION

This application claims the benefit of and priority to U.S. provisional patent application Ser. No. 62/015,073, filed 20 Jun. 2014 and having the same title, the contents of which are hereby incorporated by reference in their entirety for any and all purposes.

FIELD

This disclosure is directed to portable infusion devices, systems, and methods of using the same for dispensing effective proportions of insulin and amylin agonist, e.g., amylin analogue and amylin receptor agonist, pharmaceutical materials, and related compositions and methods.

BACKGROUND

The following includes information that may be useful in understanding the present invention. It is not an admission that any of the information, publications or documents specifically or implicitly referenced herein is prior art, or essential, to the presently described or claimed inventions. All publications and patents mentioned herein are hereby incorporated herein by reference in their entirety.

Portable infusion devices and systems have been used for dispensing compositions in the care of patients with diseases, disorders and conditions that may be treated with insulin. These devices and systems are used to dispense insulin in a controlled setting. Insulin infusion pumps are used by many people with diabetes.

Diabetes is caused by a deficiency of beta-cell hormone secretion. Sixty-five years after the discovery of insulin, a second beta-cell hormone, amylin, was discovered. Amylin is a peptide hormone that is released into the bloodstream by the β-cells of the pancreas along with insulin, after a meal. Nearly 60 different effects have been reported in various experiments using amylin (or the amylin agonist analog, pramlintide) in a variety of species. In glucose metabolism amylin's main actions conspire to control the rate of nutrient entry into plasma, in contrast with actions of insulin to accelerate nutrient disposal (e.g., into muscle and other insulin-sensitive tissues).

Given that evolution selected for two beta-cell hormones to control glucose metabolism, it has been proposed that dual hormone replacement would be optimal therapy for patients with diabetes, especially in the case of type 1 diabetes (T1D) where beta-cell function is completely gone and, like insulin, amylin is absent. See U.S. Pat. Nos. 5,124,314 and 6,136,784. Benefits reported by some patients who have used amylin replacement therapy with the compound pramlintide per its package insert instructions in addition to their insulin therapy support this hypothesis. In some of those patients, the benefits included lower HbA1c and less variability in plasma glucose levels and/or weight loss.

Pramlintide ($^{25,28,29}$Pro-h-amylin) is an agonist of amylin. Like amylin, it has been reported to aid in the absorption of glucose by slowing gastric emptying, promoting satiety, and inhibiting secretion of glucagon, a catabolic hormone that opposes the effects of insulin and amylin. E.g., Huffman D M, McLean G W, Seagrove M A (2009). "Continuous Subcutaneous Pramlintide Infusion Therapy in Patients with Type 1 Diabetes: Observations from a Pilot Study" *Endocrine Practice* 15(7): 689-695. Pramlintide has been approved by the FDA for use by T1D and type 2 diabetics (T2D) who use insulin. E.g., Ryan G J, Jobe L J, Martin R (2005). "Pramlintide in the treatment of type 1 and type 2 diabetes mellitus" *Clinical Therapeutics* 27(10): 1500-1512. Pramlintide is said to allow patients to use less insulin, to lower average blood sugar levels, and to substantially reduce what otherwise would be a large unhealthy rise in blood sugar that occurs in diabetics right after eating. Apart from insulin analogs, pramlintide is the only drug approved by the FDA to lower blood sugar in T1D since insulin in the early 1920s.

Given the number of people who need insulin, if a significant percentage of patients on insulin replacement therapy upgraded to dual hormone replacement therapy, pramlintide would be a major drug in the diabetes category. However, since its market launch pramlintide has never risen above a niche product. Two problems may have discouraged patients and caregivers. The first is multiple injections. Many patients who respond well to the drug can grow tired of pre-meal injections, and many patients who may benefit from pramlintide are put off by the idea of three more daily shots.

The second is adverse events. During the time it has been on the market, a perception has developed that pramlintide has a low therapeutic index; it does not deliver strong enough benefits to offset its downsides, particularly nausea and hypoglycemia if insulin dosing is not properly adjusted to reflect co-administration with pramlintide. Initial startup nausea is often mentioned as a concern among patients considering trial of pramlintide.

A method for the treatment of diabetes mellitus in a mammal comprising the administration of a therapeutically effective amount of pramlintide and a therapeutically effective amount of an insulin was patented nearly 20 years ago, in 1997 (U.S. Pat. No. 5,686,411 for "Amylin agonist peptides and uses therefor"). However, no such product or combination therapy was ever developed or marketed.

There remains a need in the art for new devices, methods, and therapeutics useful in treating patients having diseases, disorders, and conditions that are treated with insulin and/or amylin, or their analogues, including T1D and T2D. There is a particular need for new devices and therapeutics that span the entire spectrum of diseases, disorders, and conditions associated with amylin deficiency, particularly those that are also benefited by treatment with insulin. Such devices, methods, and therapeutics are described and claimed herein.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

This disclosure is directed to portable infusion devices, systems, and methods of using the same for dispensing and/or administering basal and bolus amylin agonist, e.g., amylin analog, pharmaceutical materials in effective proportions to dispensed and/or administered basal and bolus insulin pharmaceutical materials, and related compositions and methods. Certain embodiments of the present invention relate generally to drug infusion systems, and in particular embodiments to drug pump devices comprising a pump device, a controller for the pump device, a memory and at least one operating element for the user of the pump to operate the pump, and to a method for controlling a user interface of such a pump to deliver basal and bolus insulin and amylin agonist drugs.

In various aspects, the invention provides for administration of amylin agonist pharmaceutical materials, e.g., an amylin analog, where the amylin agonist dose is calculated as a ratio to the insulin dose and the amylin agonist/insulin ratios for basal and bolus administration of these materials are different. In one aspect, the amylin agonist/insulin basal administration ratio is greater than amylin agonist/insulin bolus administration ratio.

In another aspect, administration of an amylin analogue agonist, e.g., an amylin analog, in proportion to insulin as described herein will improve and stabilize or normalize glucose levels, distribution, and metabolism. In still another aspect, administration of an amylin analogue agonist in proportion to insulin as described herein will improve the glucagon counter-regulatory response.

In one aspect, the invention includes a medical infusion pump or pump system for delivering insulins and amylin agonists, e.g., amylin analogs and amylin receptor agonists, to patients for the purpose of improving and/or stabilizing their plasma glucose levels and/or improving their glucagon counter-regulatory responses, said pump or system comprising independent pumping mechanisms regulated by patients and/or computer-implemented algorithms that (a) set the basal and bolus rates of insulin infusion according to an individual patient's needs and (b) calculate the basal and bolus rates of amylin agonist infusion based on different basal and bolus amylin/insulin ratios, with the basal amylin/insulin basal being higher than the bolus amylin/insulin ratio.

In one aspect, the invention includes devices for dual administration of an insulin and an amylin agonist in different bolus and basal administration ratios to subjects in need of thereof. Bolus amylin agonist/insulin administration ratios and basal amylin agonist/insulin administration ratios are described herein. Ratios may adjusted, or otherwise calculated or determined, as described herein, for infusion of appropriate amounts of an amylin agonist and an insulin by multi-reservoir infusion devices or patch pumps, for example.

In various embodiments, the invention includes a programmable multiple drug chamber medical infusion pump or infusion pump system wherein (a) a processor is programmed to calculate a basal amount and delivery rate for an amylin agonist based on a predetermined basal dosing ratio of amylin agonist to basal insulin, or from a range of amylin/insulin ratios, (b) the processor is programmed to determine a bolus amount and delivery rate for said amylin agonist based on a predetermined bolus dosing ratio of amylin agonist to bolus insulin, or from a range of ratios, and (c) the processor uses these calculations to cause the pump mechanism to deliver said amylin agonist in dosing amounts and at delivery rates substantially equal to the calculated basal and bolus amounts and rates over programmed periods of time. Embodiments are directed to infusion devices or systems and methods of using these devices or systems for dispensing an insulin and an amylin agonist in particular ratios in a controllable and reliable manner. In some cases, embodiments include portable infusion pumps and infusion pump systems and methods of using such pumps for infusing, for example, multiple blood glucose-modulating amylin agonist pharmaceutical materials and insulin pharmaceutical materials, to a patient. In other cases, embodiments include the addition of devices for continuous glucose monitoring (CGM) to provide data for computerized insulin dosing algorithms that automatically adjust insulin infusion rates, i.e. closed loop insulin infusion systems. In turn, dosing algorithms may automatically adjust for infusion rates and amounts based on basal and bolus ratios following the determination, re-determination, calculation or re-calculation of insulin and/or amylin agonist administration requirements, e.g., based on fasting plasma glucose, exercise, and/or carbohydrate intake. This may include, for example, determination, re-determination, calculation or re-calculation of insulin and/or amylin analogue administration requirements following determination of an insulin carbohydrate coverage dose, a high blood sugar correction dose, a mealtime dose, and so on. Administration of appropriate doses of an insulin and an amylin analogue may also be determined or calculated as described herein for administration without a pump, e.g., by syringe or pen injection. This may especially be the case for certain insulins, e.g., those not suitable for use in a pump (such as NovoLog® Mix 70/30).

Liquid medicaments suitable for delivery to a patient by devices and methods of the invention, including by embodiments of devices and methods described herein, include bolus insulins, basal insulins, and amylin agonists, such as amylin analogues for example. As described herein, amongst other things, amylin agonists include amylins, e.g., a human or rodent amylin, amylin receptor agonists and amylin analogues, e.g., pramlintide.

In one aspect, the invention includes a programmable multiple drug chamber medical infusion pump or infusion pump system including a pumping mechanism and a processor, wherein (a) the processor is programmed to calculate a basal amount and delivery rate for delivery of an amylin agonist based on a predetermined basal dosing ratio of the amylin agonist to basal insulin, or range or ratios, wherein the amount and delivery rate are automatically adjusted based on the amount of insulin selected by the user for administration, (b) the processor is programmed to calculate a bolus delivery rate for an amylin agonist based on a predetermined bolus dosing ratio of amylin agonist to bolus insulin, wherein the amount and delivery rate are automatically adjusted based on the amount of insulin selected by the user for administration, and (c) the processor uses these calculations to cause the pumping mechanism to deliver the amylin agonist in dosing amounts and at delivery rates substantially equal to the calculated basal and bolus amounts and rates over programmed periods of time.

In another aspect, the invention includes a programmable medical infusion pump or infusion pump system having a data input device (internal and/or external), said pump comprising an amylin agonist drug reservoir, an insulin drug reservoir, one or more pump mechanisms, and a processor in data communication with a data input device and arranged to control the pump mechanism(s), wherein the processor is programmed (a) to deliver a basal insulin amount from the insulin drug reservoir, (b) to deliver an amylin agonist from the amylin agonist drug reservoir at a basal rate to a user by prompting the user to select a basal insulin infusion rate or by referencing a preselected basal insulin infusion rate, (c) calculating an amount and delivery rate for the amylin agonist based on a predetermined ratio of basal amylin agonist to the basal insulin over a predetermined period of time, and (d) to control a pump mechanism to deliver the amylin agonist from the drug reservoir at a delivery rate substantially equal to the calculated basal rate during the period of time.

In one embodiment, the data input device is a keypad or touchscreen or other user interface, for example. In another embodiment the data input device is a smart phone. In another embodiment the data input device is a keypad or touchscreen or other user interface that also works in conjunction with a smart phone, e.g., via a Bluetooth® connection. Other data input devices may be used.

In one embodiment, the drug reservoir is a cartridge.

In yet another aspect, the invention includes a medical infusion pump or infusion pump system containing a pharmaceutical formulation comprising an amylin agonist and a pharmaceutical formulation comprising an insulin, and the pump is programmed to administer the amylin agonist and the insulin to a subject in an amount and frequency to provide a basal level of the insulin and to provide a basal plasma level of the amylin agonist over a 24-hour period wherein the basal plasma level of the amylin agonist provided over the 24-hour period is equal to from between about 7% to about 15% of the basal level of insulin provided over the same period, and, optionally, programmed to administer a mealtime bolus of insulin and to administer a mealtime bolus of an amylin agonist wherein the amylin agonist is administered one or more times per day in an amount and frequency to provide a mealtime bolus of the amylin agonist to the subject that is equal to from between about 2% to about 5% of the mealtime bolus amount of an insulin administered to the subject.

In yet another aspect, the invention includes a programmable medical infusion pump or infusion pump system having a data input device (internal and/or external), where the pump comprises an amylin agonist drug reservoir, an insulin drug reservoir, one or more pump mechanisms, and a processor in data communication with a data input device and arranged to control the pump mechanism, and wherein the processor is programmed to (a) deliver a mealtime bolus amount of an insulin from the insulin drug reservoir, (b) to deliver a mealtime bolus amount of an amylin agonist from the amylin agonist drug reservoir to a user by prompting the user to select a mealtime bolus amount of an insulin or by referencing a preselected mealtime insulin bolus amount and infusion rate, (c) calculating an amount and delivery rate for the amylin agonist based on a predetermined ratio of the mealtime amylin agonist bolus to the mealtime insulin bolus over a predetermined period of time, and (d) controlling the pump mechanism to deliver the amylin agonist from the drug reservoir at a delivery rate substantially equal to the calculated mealtime bolus during the period of time.

In yet another aspect, the invention includes a programmable medical infusion pump or infusion pump system having an internal and/or external data input device, where the pump comprises an amylin agonist drug reservoir, an insulin drug reservoir, one or more pump mechanisms, and a processor in data communication with a data input device and arranged to control the pump mechanism, and wherein the processor is programmed to (a) deliver a basal amount of an insulin and a mealtime bolus amount of an insulin to a user from the insulin drug reservoir, (b) to deliver a basal amount of an amylin agonist and a mealtime bolus amount of an amylin agonist from the amylin agonist drug reservoir to a user by prompting the user to select a basal amount of an insulin and a mealtime bolus amount of an insulin, as appropriate or desired, or by referencing a preselected basal amount of an insulin or a mealtime insulin bolus amount and infusion rate, (c) calculating an amount and delivery rate for the amylin agonist based on different predetermined ratios or from different ranges of ratios of (i) a basal amount of an amylin agonist to the basal amount of an insulin over a predetermined period of time and (ii) a mealtime amylin agonist bolus to a mealtime insulin bolus over a predetermined period of time, and (d) controlling the pump mechanism to deliver the amylin agonist from the drug reservoir at delivery rates substantially equal to the calculated basal amount and mealtime bolus amount(s) during the period(s) of time. In particularly preferred embodiments, the amount and delivery rate for the amylin analogue is calculated based on different predetermined ratios or from different ranges of ratios such that the basal amylin/insulin ratio is higher than the bolus amylin/insulin ratio.

Various ratios may be used to determine the amounts of an amylin agonist, e.g. an amylin analogue, and an insulin to be administered. They include an in vivo molar ratio, an in vivo gram ratio (adjusted for molecular weight), an ex vivo gram ratio (adjusted for bioavailability), and an ex vivo μg/U ratio (for convenience in using insulin). The amounts may be based on area under the curve (AUC) measurements.

In another aspect, the amylin agonist provided the medical infusion pump or infusion pump system is pramlintide, and the pump is programmed (a) to administer pramlintide to a subject in an amount and frequency to provide a basal pramlintide level over a 24-hour period that is equal to about 15% of the basal insulin level provided, and (b) to administer a mealtime bolus of pramlintide one or more times per day in an amount and frequency to provide a mealtime bolus of pramlintide to the subject that is equal to about 5% of a mealtime bolus amount of the insulin administered to the subject.

In another aspect, the programmable medical infusion pump or infusion pump system includes a processor that is programmed to calculate a basal amount of an amylin agonist and to deliver the amylin agonist from a drug reservoir at a basal rate by comparing the pharmacokinetics of the amylin agonist and the insulin in order to maintain a basal plasma level of the amylin agonist that is from about 7% to about 15% or from about 5% to about 22% of the basal plasma levels of the insulin, measured on a molar basis. In one aspect, the in vivo gram ratio (adjusted for molecular weight) ranges from about 3% to about 15%. In yet another aspect, rather than in vivo molar ratios, the programmable medical infusion pump or infusion pump system includes a processor that is programmed to calculate a basal amount of an amylin agonist and to deliver the amylin agonist from a drug reservoir at a basal rate by comparing the ex vivo gram ratios of the amylin agonist and the insulin in order to provide an amount of the amylin agonist that is from about 6% to about 30% of the amount of the insulin. In yet another aspect, the programmable medical infusion pump or infusion pump system includes a processor that is programmed to calculate a basal amount of an amylin agonist and to deliver the amylin agonist from a drug reservoir at a basal rate by comparing the ex vivo μg/U ratio (for convenience in using insulin) of the amylin agonist and the insulin in order to provide a basal amount of the amylin agonist that is from about 2 micrograms of the amylin agonist to 1 Unit of the basal insulin to about 11 micrograms of the amylin agonist to 1 Unit of the basal insulin. The amylin agonist, in one embodiment, is pramlintide.

In yet another aspect, the programmable medical infusion pump or infusion pump system includes a processor that is programmed to calculate or determine and deliver a bolus amount of an amylin agonist by comparing the pharmacokinetics of the amylin agonist and an insulin in order to deliver a bolus of the amylin agonist to yield a plasma level that is from about 2% to about 5% or from about 2% to about 7% of the plasma level resulting from the bolus administration of the insulin, measured on a molar basis. In one aspect, the in vivo gram ratio (adjusted for molecular weight) ranges from about 1% to about 5%. In yet another aspect, rather than in vivo molar ratios, the programmable medical infusion pump or infusion pump system includes a processor that is programmed to calculate and deliver a bolus amount of an amylin agonist from a drug reservoir by comparing the ex vivo gram ratios of the amylin agonist and the insulin in order to provide an amount of the amylin agonist that is from about 2% to about 10% of the amount of the insulin. In yet another aspect, the programmable medical infusion pump or infusion pump system includes a processor that is programmed to calculate a bolus amount of an amylin agonist and to deliver the amylin agonist from a drug reservoir at a bolus rate by comparing the ex vivo µg/U ratio (for convenience in using insulin) of the amylin agonist and the insulin in order to provide a bolus amount of the amylin agonist that is from about 1 microgram of the amylin agonist to 1 Unit of the bolus insulin to about 4 micrograms of the amylin agonist to 1 Unit of the basal insulin. The amylin agonist, in one embodiment, is pramlintide.

In another aspect, the programmable medical infusion pump or infusion pump system includes a processor that is programmed to calculate the basal amount of an amylin agonist to be delivered by further evaluating one or more dosing parameters selected from the group consisting of, for example, mean or median values of amylin agonist/insulin ratios generated from clinical studies, and ranges thereof; subject age; subject body mass index; expected levels of glucagon secretion; subject exercise; and, subject diet.

In another aspect, the invention includes a programmable medical infusion pump or infusion pump system, wherein the processor is programmed to receive data specifying a bolus amount of an amylin agonist and/or an insulin, the duration of administration of the bolus amount(s), the portion of the bolus amount(s) to be delivered immediately upon executing a deliver command and a remainder of the bolus amount(s) to deliver over the duration upon executing a deliver command, thereby controlling the pump mechanism to deliver the bolus.

The present invention also includes methods. In one aspect, the invention includes a method for treating an insulin-using subject with an amylin agonist, comprising the administration of basal and bolus amounts of an amylin agonist composition that are determined by two different dosing ratios that take into account the insulin basal and bolus amounts administered by the subject. The invention includes methods and therapeutics for dual administration of an insulin and an amylin agonist, e.g. an amylin analogue, in different bolus and basal administration ratios to subjects in need of thereof. Bolus amylin/insulin administration ratios and basal amylin/insulin administration ratios are described herein. Ratios may adjusted, or otherwise calculated or determined, as described herein. In particularly embodiments, the basal amylin/insulin ratio is higher than the bolus amylin/insulin ratio.

In another aspect, the invention is directed to a method of administering to humans an amylin agonist in combination with insulin in a fashion that does not cause nausea and achieves maximum glucose control efficacy.

In other embodiments, the invention includes methods of calculating the dose of an amylin agonist to be administered based on two components, whereby a first amylin agonist dose is determined by considering a patient's basal dosing of insulin and a second amylin agonist dose is determined by considering a patient's bolus dosing of insulin.

In still other embodiments, the invention includes methods of treating diabetes and other glucose-handling disorders characterized at least in part by hyperglycemia, using a dual chamber hormone or drug pump programmed to calculate the proper infusion rate of an amylin agonist based on two components, whereby the first portion is determined using a patient's basal infusion rate of insulin and the second portion is determined using a patient's bolus infusions of insulin.

In various embodiments, an alternative to a dual chamber or multi-reservoir drug pump is the use of two patch pumps under unified electronic control, e.g., with a smart phone or smart watch or the like. A patch pump has a drug reservoir, a drug pumping mechanism, a cannula for delivering drug subcutaneously, and, preferably, a receiver/transmitter to permit wireless connection to an electronic control module. The most widely used patch pump system today is the OmniPod by Insulet, which consists of a disposable Pod that is worn for three days and a Personal Diabetes Monitor (PDM). The PDM communicates wirelessly with the Pod to program basal insulin infusion rates and to activate bolus doses; it also has an onboard glucose meter that analyzes finger prick blood samples. In addition to eliminating tubing connections, a pair of patch pumps may be located at two different infusion sites, thereby avoiding any potential interference between insulin and amylin agonist infusions. This separation would be especially important during clinical research to evaluate optimal insulin/amylin dosing algorithms, since such research may be initiated without first confirming that two hormones could safely and effectively be delivered via a single subcutaneous cannula.

In another aspect, the invention includes a pre-programmed machine, e.g. a pre-programmed pump or dual pump or pump system, or a pre-programmed patch pump control, to control the delivery of an amylin agonist, e.g., an amylin analog, and an insulin in predetermined ratios, such as are described herein for basal and bolus administration.

In other embodiments, the invention includes formulations combining insulin and an amylin agonist in different ratios, as described or calculated herein, based upon whether the formulation is for basal or for bolus dosing.

In one embodiment of the present invention, for example, an amylin agonist is infused such that on a weight-of-drug basis the basal component is greater than the bolus component of total daily dosing. In another embodiment of the present invention, the sizes of an amylin agonist basal rate and bolus doses to be infused are calculated based on defined ratios to the insulin basal rate and bolus doses. In yet another embodiment of the present invention, an amylin agonist and insulin are infused by a dual or multiple chamber pump, or by patch pumps, which is/are programmed to deliver predetermined or calculated ratios of insulin and amylin agonist basal rates and mealtime boluses depending upon the individual patient's insulin regimen, as summarized herein.

In one aspect, the methods are for treating an insulin-using subject with an amylin agonist comprising basal and bolus amylin agonist components which are determined by two different dosing ratios to the insulin basal and bolus components.

In another aspect, a method for treating an insulin-using subject with an amylin agonist is provided that comprises administering an amylin agonist to said subject in an amount and frequency to provide a basal plasma level of said amylin agonist over a 24-hour period in a pre-determined ratio to the basal level of an insulin administered to said subject. The insulin may be a basal or long-acting insulin. The amount of basal amylin agonist administered over said period may be equal to, for example, from between about 7% to about 15% of a basal level of an insulin administered to said subject, or other ratios as described or referenced herein. In one aspect, the amount of amylin agonist administered over said period is about 10% to about 15% of the amount of a basal or long-acting insulin during the period of time. In another aspect, the amount of amylin agonist administered over the 24-hour period is about 15% of the amount of a basal or long-acting insulin during the period. In another aspect, the method further comprises administering an amylin agonist one or more times per day in an amount and frequency to provide a mealtime bolus of said amylin agonist in a pre-determined ratio to the bolus amount of an insulin administered to said subject, wherein the pre-determined ratio to said bolus amount is different from and lower than the pre-determined ratio of a basal amount of an amylin agonist to the basal amount of an insulin administered to said subject. In one aspect, the pre-determined ratio of the amount of said amylin agonist provided as a bolus to the amount of an insulin administered as a bolus to said subject is equal to from between about 2% to about 5% or from about 2% to about 7% of a mealtime bolus amount of an insulin administered to said subject, or other ratios as described or referenced herein, including in vivo molar ratios, in vivo gram ratios (adjusted for molecular weight), ex vivo gram ratios (adjusted for bioavailability), and ex vivo μg/U ratios (for convenience in using insulin).

In another aspect, a method for treating an insulin-using subject with an amylin agonist is provided that comprises administering an amylin agonist to a subject in an amount and frequency to provide a basal plasma level of said amylin agonist over a 24-hour period in a pre-determined ratio to the basal level of an insulin administered to the subject over the same period of time, and where that ratio is different from and higher than the ratio of an amylin agonist to an insulin to be administered as a bolus, for example, as a mealtime bolus.

In one aspect, the amylin agonist is an amylin. In another aspect, the amylin agonist is a derivative of an amylin. In another aspect, the amylin agonist is an agonist analog of an amylin, for example, human amylin or rat amylin. In another aspect, the amylin agonist is pramlintide.

In one aspect, the insulin is a basal or long-acting insulin. In another aspect, the insulin is a bolus or short-acting insulin.

In one aspect, the amylin agonist (e.g., an amylin analogue) is administered to a subject in conjunction with insulin. In another aspect, the amylin agonist is pramlintide and it is administered with a basal or a long-acting insulin. In another aspect, the amylin agonist is pramlintide and it is administered with a bolus or a short-acting insulin.

In one aspect, the amylin agonist administered to provide a basal level of amylin agonist and the amylin agonist administered as a mealtime bolus of said amylin agonist is pramlintide.

In one aspect, the amylin agonist and/or the insulin is administered to a subject by injection.

In another aspect, the amylin agonist and/or the insulin is/are administered to a subject by infusion. In yet another aspect, the amylin agonist and/or the insulin is/are administered to a subject by subcutaneous continuous infusion.

In one aspect, the amylin agonist and/or the insulin is/are administered to a subject by a medical infusion pump or infusion pump system. In another aspect, the amylin agonist and/or the insulin are administered to a subject by subcutaneous continuous infusion from a programmable medical infusion pump or infusion pump system.

In one aspect, the subject has a glucose-handling disorder. In one aspect the glucose-handling disorder is any disease, condition or disorder that may be treated with insulin and/or an amylin agonist. In one aspect, the glucose-handling disorder is diabetes. In one aspect, the diabetes Type 1 diabetes. In another aspect, the diabetes is Type 2 diabetes.

In another aspect, the invention includes methods for treating a subject for hyperglycemia, comprising (a) administering an amylin agonist to the subject in an amount and frequency to provide a basal plasma level of the amylin agonist over a 24-hour period that is equal to, for example, from between about 7% to about 15% of a basal level of an insulin administered to the subject, or some other predetermined or calculated ratio (which may be referred to as a first predetermined ratio), and (b) administering an amylin agonist to the subject one or more times per day in an amount and frequency to provide a mealtime bolus of the amylin agonist that is equal to from between about 2% to about 5% of a mealtime bolus amount of an insulin administered to the subject, or some other predetermined or calculated ratio (which may be referred to as a second predetermined ratio), wherein the first predetermined ratio is higher than and different from and higher than the second predetermined ratio. Other basal and bolus amylin agonist/insulin ratios are described or referenced herein, or may be calculated as described herein, for use in the methods of the invention.

In another aspect, the invention includes a commercial package containing a pharmaceutical formulation containing an amylin agonist for parenteral administration to an insulin-using subject, and the package comprises instructions for administering the amylin agonist in an amount and frequency to provide a basal plasma level of said amylin agonist over a 24-hour period as described herein, for example, in an amount and frequency that is equal to from between about 7% to about 15% of a basal level of an insulin to be administered to said subject, or in some other predetermined or calculated ratio. In another aspect, the commercial package further comprises instructions for administering an amylin agonist one or more times per day as described herein, for example, in an amount and frequency to provide a mealtime bolus of the amylin agonist that is equal to from between about 2% to about 5% of a mealtime bolus amount of an insulin to be administered to said subject, or in some other predetermined or calculated ratio. Other basal and bolus amylin agonist/insulin ratios that are described or referenced herein, or may be calculated as described herein, may be included or referenced in the commercial package of the invention.

In another aspect, the amylin agonist included in the commercial package for bolus administration is pramlintide.

In one aspect, the amylin agonist included in the commercial package for basal administration is a long-acting amylin agonist.

In one aspect, the amylin agonist included in the commercial package for basal administration is pramlintide. In a related aspect, the amylin agonist included in the commercial package for basal administration is pramlintide, and the instructions provide that the basal plasma level of pramlintide to be administered over a 24-hour period is equal to about 15% of the basal level of an insulin to be administered to said subject over the 24-hour period, or some other predetermined or calculated amount. In another aspect, the amylin agonist in the commercial package to be administered as a mealtime bolus is pramlintide, and the amount of pramlintide to be administered as a mealtime bolus is equal to about 5% of the amount of an insulin to be administered as a mealtime bolus to said subject, or some other predetermined or calculated amount as described or referenced herein.

In one aspect, the invention includes pharmaceutical compositions for administration to a subject comprising a basal blend of an insulin and an amylin agonist, where the amylin agonist and the insulin are present in a ratio ranging from about 1:14 to about 1:6 or 1:7, or in another predetermined or calculated ratio as described or referenced herein. In one aspect the amylin agonist in the pharmaceutical composition is pramlintide and the insulin is a basal or long-acting insulin. In another aspect the amylin agonist in the pharmaceutical composition is long-acting amylin agonist and the insulin is a basal or long-acting insulin.

In another aspect, the invention includes pharmaceutical compositions for administration to a subject comprising a bolus blend of an insulin and an amylin agonist, where the amylin agonist and the insulin are present in a ratio ranging from about 1:50 to about 1:20, or in another predetermined or calculated ratio as described or referenced herein. In one aspect the amylin agonist in the pharmaceutical composition is pramlintide and the insulin is a bolus or short-acting insulin. In another aspect the amylin agonist in the pharmaceutical composition is short-acting amylin agonist and the insulin is a bolus or short-acting insulin present in ratios disclosed or calculated as described herein.

In one aspect, the compositions are useful for the treatment of disorders that can be ameliorated by administration of insulin and/or amylin, or their agonists. In another aspect, the inventions include compositions comprising or consisting essentially of each of these compounds in predetermined ratios for basal administration and bolus administration that are different from each other. In another aspect, the ratio of an amylin agonist to an insulin for basal administration is higher than the ratio of an amylin agonist to an insulin for bolus administration.

The invention includes a pharmaceutical composition comprising one or more pharmaceutically acceptable insulin and amylin agents for the treatment of a glucose disorder, e.g., T1D, T2D, etc., and related diseases, disorders and conditions characterized at least in part by insulin and/or amylin deficiency. Thus, the inventions include pharmaceutical compositions in a form suitable for, or adapted to, treatment of a subject for a such diseases, disorders or conditions. In one embodiment, the disease, disorder or condition is associated with dysglycemia. In certain embodiments, the disease, disorder or condition is any form of diabetes. The form of diabetes may, for example, be T1D. In other embodiments, the disease, disorder or condition is T2D, particularly insulin-using T2D.

In one aspect, the pharmaceutical compositions are formulated for intravenous administration, including by infusion or as a bolus. Administration may be, for example, by subcutaneous or intramuscular injection or by means of a pump, for example a pre-programmed or programmable pump.

The amylin agonist and the amylin agonist/insulin pharmaceutical compositions of the invention, and for use in the methods of the invention, may formulated for cartridges.

Pharmaceutical compositions according to the present invention may be administered parenterally to patients in need of such a treatment. Parenteral administration may be performed by injection, preferably subcutaneous or intramuscular injection by means of a syringe, optionally a pen-like syringe, or mechanical driven injector. Alternatively, parenteral administration can be performed by means of an infusion pump or infusion pump system.

In another aspect, the compositions of the invention comprise an amylin and an insulin in basal ratios as provided herein, an amylin and an insulin in bolus ratios as provided herein, or in basal or bolus ratios calculated based on the discoveries and description herein. These compositions and amounts may be provided as single or multiple doses.

In one embodiment, the amylin agonist is administered in a single dose. In another embodiment, the amylin agonist is administered in more than one dose. In yet another embodiment, the amylin agonist is administered continuously over a period of time, for example a predetermined period of time. In still another embodiment, insulin or an agonist or analog thereof is co-administered with the amylin agonist.

In another aspect, the treated subject is a mammal, preferably a human. Other mammals include domestic and farm animals, and zoo, sports, or pet animals, such as dogs, horses, and cats.

The inventions include a combined fluid injection and control system and includes a fluid delivery system including at least one pumping device, a fluid path, and a control unit. The fluid path is adapted to connect the pumping device to a patient via, for example, a cannula inserted in the patient. The control unit is operable to control the fluid delivery system. In operation, the control unit selectively actuates the fluid delivery system to operate in a fluid injection mode. In the fluid injection mode the pumping device delivers fluid to the fluid path for a fluid injection procedure. An operator control may be connected to the control unit for controlling the fluid delivery system and may be a handheld device.

It will be understood that the inventions include pumps programed to deliver an amount of an amylin agonist in a predetermined or calculated ratio to an amount of a bolus or short-acting insulin and/or a basal or long-acting insulin. In one embodiment the amylin agonist is pramlintide.

It will be understood that the devices, compositions and methods of the invention for the treatment of a glucose disorder, or any other diseases, disorders and conditions involving treatment with an insulin and an amylin agonist are disclosed.

Treatment of a subject as provided herein with one or more compounds or pharmaceutical compositions as described herein may comprise their simultaneous, separate, sequential or sustained administration.

Pharmaceutical compositions useful for preventing and/or treating a glucose-handling disorder, e.g., diabetes, hyperglycemia, and related diseases, disorders and conditions involving treatment with insulin and/or amylin, are also provided in the form of a combined preparation, for example, as an admixture of two or more amylin agonists with or without an insulin.

The term "a combined preparation" includes not only physical combinations of compounds, but compounds provided as a "kit of parts" in the sense that the combination partners as defined above can be dosed independently or by use of different fixed combinations with distinguished amounts of the combination partners (a) and (b), i.e. simultaneously, separately or sequentially. The parts of the kit can then, for example, be administered simultaneously or chronologically staggered, that is at different time points and with equal or different time intervals for any part of the kit of parts.

In one embodiment, the inventions include a kit comprising one or more doses of an amylin agonist, the kit comprising one or more of a syringe, a "pen" injector that delivers a metered dose, a needle-less injector, a liquid formulation, a lyophilized powder and a sterile liquid for reconstitution. In one embodiment a combined preparation is administered, wherein two or more separate compositions are administered to a subject, wherein the first composition comprises a therapeutically effective amount of an amylin, e.g., an amylin agonist, and the second composition comprises a therapeutically effective amount of an insulin.

Methods of the invention include the sequential or simultaneous administration a an amylin agonist, and an insulin as described herein, wherein the insulin is administered in amounts or doses that are less that those used when the insulin are administered alone, i.e., when it not administered together or in combination with an amylin agonist. Such lesser amounts of insulin administered is typically taken from the bolus doses, which are about 5-25% less, for example, than the amount or amounts of insulin bolus doses when administered without an amylin agonist.

In another aspect, the invention includes an article of manufacture comprising a vessel containing a therapeutically effective amount of an amylin agonist(s), such as, for example, pramlintide, and instructions for use, including use for the treatment of a subject as described herein. The invention includes a article of manufacture comprising packaging material containing one or more dosage forms as described herein, wherein the packaging material has a label that indicates that the dosage form can be used for a subject having or suspected of having or predisposed to any of the diseases, disorders and/or conditions described or referenced herein, including T1D and T2D and hyperglycemias.

The invention includes method of preparing a medicament for preventing and/or treating a glucose-handling disorder as described herein, e.g., diabetes or hyperglycemia, comprising bringing together and an amount of an amylin agonist, and a pharmaceutically acceptable carrier together with one or more insulins useful for a glucose-handling disorder as described herein, e.g., diabetes or hyperglycemia.

The invention includes methods for the use of a therapeutically effective amount of an amylin agonist, in the manufacture of a dosage form useful for preventing and/or treating a glucose-handling disorder as described herein, e.g., diabetes or hyperglycemia. Such dosage forms include, for example, parenteral delivery forms and formulations, well as other forms of delivery including forms for delivery by infusion, injection and instillation, and related compositions and devices, for example. Such dosage forms include those for the treatment of a subject as disclosed herein.

In certain other aspect, the invention provides a package comprising an amylin agonist, together with instructions for use in combination with one or more insulins for preventing and/or treating a glucose-handling disorder as described herein, e.g., diabetes or hyperglycemia.

In other aspects, the inventions provide for use of one or more of the compounds and compositions described herein in the manufacture of a medicament. In other aspects, the inventions provide for use of one or more of the compounds and compositions described herein in the manufacture of a medicament for use in the treatment of one or more of the diseases, disorders and conditions described herein. In other aspects, the inventions provide for use of one or more of the compounds, compositions and medicaments described and claimed herein in the treatment of a subject for one or more of the diseases, disorders and conditions described herein.

These and other aspects of the present inventions, which are not limited to or by the information in this Brief Summary, are provided below, including in the claims.

Briefly, the description and the claims concern certain aspects of the invention. Some of these aspects concern medical infusion pumps or infusion pump systems, particularly those that are programmable. In one such aspect of such programmable medical infusion pumps or infusion pump systems, the devices include a user interface, e.g., a touchscreen, a drug reservoir, a drug pump, a data input device, and a processor in data communication with the user interface that is configured to control the drug pump. The processor is programmed to deliver to the user an amylin agonist from the device's drug reservoir at a differential basal rate and a bolus rate by prompting the user to select a basal or bolus insulin infusion rate or by referencing a preselected basal or bolus insulin infusion rate, calculating a delivery rate for the amylin agonist based on a predetermined ratio of basal or bolus amylin agonist to the basal or bolus insulin over a predetermined period of time, and controlling the drug pump to deliver the amylin agonist from the drug reservoir at a delivery rate substantially equal to the calculated basal or bolus rate during the period of time.

In another aspect, in some embodiments the programmable medical infusion pump or infusion pump system includes a drug pump, a data input device, and a processor in data communication with a touchscreen and configured to control the drug pump. In such devices, the processor is programmed to (a) deliver an amylin agonist at a basal rate to a user by prompting the user to select a basal insulin infusion rate or by referencing a preselected basal insulin infusion rate, calculate a delivery rate for the amylin agonist based on a predetermined ratio of basal amylin agonist to the basal insulin over a predetermined period of time, (b) deliver a mealtime bolus amount of an amylin agonist to the device's user by prompting her/him to select a mealtime bolus amount of an insulin or by referencing a preselected mealtime insulin bolus amount and infusion rate, calculate a delivery rate for the amylin agonist based on a predetermined ratio of said mealtime amylin agonist bolus to the mealtime insulin bolus over a predetermined period of time, and (c) deliver the amylin agonist in amounts and at delivery rates substantially equal to the calculated basal amount and rate and the calculated mealtime bolus amount over the predetermined periods of time.

In still another aspect, in some embodiments the programmable medical infusion pump or infusion pump system includes a keypad or touchscreen, an amylin agonist drug reservoir, an insulin drug reservoir, one or more drug pumps, a data input device, and a processor in data communication with the keypad or touchscreen that is configured to control the drug pump(s). The processor is programed to (a) deliver a basal insulin amount from the insulin drug reservoir, (b) deliver an amylin agonist from the amylin agonist drug reservoir at a basal rate to a user by prompting the user to select a basal insulin infusion rate or by referencing a preselected basal insulin infusion rate, calculate a delivery rate for the amylin agonist based on a predetermined ratio of basal amylin agonist to the basal insulin over a predetermined period of time, and (c) control the particular drug pump to deliver the amylin agonist from the corresponding drug reservoir at a delivery rate substantially equal to the calculated basal rate during the period of time.

In embodiments of yet another aspect that concerns programmable medical infusion pumps or infusion pump systems, such devices have a keypad or touchscreen, an amylin agonist drug reservoir, an insulin drug reservoir, one or more drug pumps, a data input device, and a processor in data communication with the keypad or touchscreen that is configured to control the drug pumps. The processor of such devices is programmed (a) to deliver to the device's user a mealtime bolus amount of an insulin from the insulin drug reservoir, (b) to deliver to the device's user a mealtime bolus amount of an amylin agonist from the amylin agonist drug reservoir by prompting the user to select a mealtime bolus amount of an insulin or by referencing a preselected mealtime insulin bolus amount and infusion rate, calculate a delivery rate for the amylin agonist based on a predetermined ratio of the mealtime amylin agonist bolus to the mealtime insulin bolus over a predetermined period of time, and (c) control the drug pump to deliver the amylin agonist from the corresponding drug reservoir at a delivery rate substantially equal to the calculated mealtime bolus during the period of time.

In embodiments of still another aspect, the invention provides medical infusion pumps or infusion pump systems that contain a pharmaceutical formulation that includes an amylin agonist and an insulin-containing pharmaceutical formulation. Such devices are programmed to administer an amylin agonist and an insulin to a subject in an amount and at a frequency that provides a basal level of insulin and a basal plasma level of an amylin agonist over a 24-hour period that is equal to from between about 7% to about 15% of the basal level of insulin. In some of these embodiments, the device is programed to administer a mealtime bolus of insulin and a mealtime bolus of an amylin agonist, where the amylin agonist is administered one or more times per day in an amount and at a frequency that provides a mealtime bolus of the amylin agonist that is equal to from between about 2% to about 5% of the mealtime bolus amount of insulin administered to the subject. In some particularly preferred embodiments the amylin agonist is pramlintide, and the pump is programmed to administer to the subject (a) pramlintide in an amount and at a frequency that provides a basal pramlintide level over a 24-hour period that is equal to about 15% of the basal insulin level administered to the subject, and (b) a mealtime bolus of pramlintide one or more times per day in an amount and at a frequency that provides a mealtime bolus of pramlintide to the subject that is equal to about 5% of the mealtime bolus amount of insulin administered to the subject.

Some embodiments of this aspect include infusion pumps or infusion pump systems that are programmable and also include at least one of the following:

a. the molar ratio of basal amylin agonist to basal insulin is about 1:6 or 1:7;

b. the amylin agonist is pramlintide, the insulin is a short-acting insulin, and the ratio of basal pramlintide to basal insulin infusion is from about 1:14 to about 1:6 or 1:7;

the drug pump is configured to administer an amylin agonist from a drug reservoir by continuous subcutaneous infusion;

the user interface is a keypad or touchscreen;

the ratio of bolus amylin agonist to bolus insulin is about 1:20;

the amylin agonist is pramlintide, the insulin is a long-acting insulin, and the ratio of basal pramlintide to basal insulin infusion is from about 1:50 to about 1:20;

a user interface that is a smart phone or smart watch, or other smart device, for example, which may be portable, transportable, or wearable;

the processor is programmed to calculate a basal amount of an amylin agonist and to deliver said amylin agonist from said drug reservoir at a basal rate by comparing the pharmacokinetics of said amylin agonist and an insulin in order to maintain a basal plasma level of said amylin agonist that is from about 7% to about 15% or from about 5% to 22% of the basal plasma levels of said insulin;

the processor is programmed to calculate and deliver a bolus amount of an amylin agonist by comparing the pharmacokinetics of said amylin agonist and an insulin in order to deliver a bolus of said amylin agonist to yield a plasma level that is from about 2% to 5% or from about 2% to about 7% of the plasma level resulting from said bolus administration of said insulin;

the processor is programmed to calculate the basal amount of an amylin agonist to be delivered by further evaluating one or more dosing parameters selected from the group consisting of mean or median values of amylin agonist/insulin ratios generated from clinical studies, and ranges thereof; subject age; subject body mass index; expected levels of glucagon secretion; subject exercise; and, subject diet; and the processor is programmed to receive data specifying a bolus amount, the duration of administration of the bolus amount, the portion of the bolus amount to be delivered immediately upon executing a deliver command and a remainder of the bolus amount to deliver over the duration upon executing a deliver command, and execute the deliver command thereby controlling the drug pump to deliver the bolus.

Other aspects of the invention relate to methods for treating an insulin-using subject with an amylin agonist and methods of treating hyperglycemia. With regard to methods for treating an insulin-using subject with an amylin agonist, some embodiments include administering an amylin agonist to a subject in an amount and at a frequency that provides a basal plasma level of the amylin agonist over a 24-hour period that is equal to from between about 7% to about 15% of a basal plasma level of an insulin administered to that subject, as well as administering one or more times per day to that subject an amylin agonist in an amount and at a frequency that provides a mealtime bolus of the amylin agonist that is equal to from between about 2% to about 5% of the mealtime bolus amount of insulin administered to that subject.

In a related aspect, the invention provides methods of treating hyperglycemia. Such methods include (a) administering an amylin agonist in an amount and frequency to provide a basal plasma level of said amylin agonist over a 24-hour period that is equal to from between about 7% to about 15% of a basal level of an insulin administered to the subject, and (b) administering an amylin agonist one or more times per day in an amount and at a frequency that provides a mealtime bolus of the amylin agonist that is equal to from between about 2% to about 5% of a mealtime bolus amount of an insulin administered to the subject.

Some embodiments of this aspect concern methods that include or further include at least one of the following: the amylin agonist is a derivative of amylin; the amylin agonist is an agonist analog of amylin; the amylin agonist is pramlintide; the amylin agonist is administered in conjunction with insulin; the amylin agonist administered to provide a basal level of amylin agonist and the amylin agonist administered as a mealtime bolus of said amylin agonist is pramlintide; the insulin administered with the bolus amylin agonist is a short-acting insulin; the insulin administered with the basal amylin agonist is a long-acting insulin; the insulin administered to provide a basal level of insulin and the insulin administered as a mealtime bolus is a short-acting insulin and a long-acting insulin, respectively; the amylin agonist is administered by injection; the amylin agonist is administered by infusion; the amylin agonist is administered by infusion from a medical infusion pump or infusion pump system; the amylin agonist is administered by subcutaneous continuous infusion; the amylin agonist is administered by subcutaneous infusion; the amylin agonist and the insulin are administered by subcutaneous continuous infusion; the amylin agonist and the insulin are administered by subcutaneous infusion; the amylin agonist and the insulin are administered by subcutaneous continuous infusion from a programmable medical infusion pump or infusion pump system; the bolus amylin agonist and the bolus insulin are administered by subcutaneous infusion from a programmable medical infusion pump or infusion pump system; the subject is a human; the subject has Type 1 diabetes; the subject has Type 2 diabetes.

Still other aspects of the invention concern articles of manufacture. Some of these aspects concern pharmaceutical compositions, whereas others relate to kits or commercial packages.

With regard to pharmaceutical compositions, one aspect concerns pharmaceutical compositions for administration to a subject that include a basal blend of an insulin and an amylin agonist, preferably where the amylin agonist and insulin are present in a ratio ranging from about 1:14 to about 1:6 or 1:7. In a related aspect, the amylin agonist and insulin are present in the pharmaceutical compositions in a ratio of about 1:6. In a related aspect, the and insulin are present in the pharmaceutical compositions in a ratio of about 1:7. In a related aspect, the and insulin are present in the pharmaceutical compositions in a ratio of between about 1:6 and 1:7.

Another aspect that concerns pharmaceutical compositions relates to pharmaceutical compositions for administration to a subject that include basal blends of a long-acting insulin and pramlintide.

Yet another aspect that concerns pharmaceutical compositions relates to pharmaceutical compositions for administration to a subject that include a basal blend of a long-acting insulin and pramlintide.

Another aspect that relates to pharmaceutical compositions concerns those that have a bolus blend of an insulin and an amylin agonist, with the amylin agonist and insulin preferably being present in a ratio ranging from about 1:50 to about 1:20. A related aspect involves bolus blends of an insulin and an amylin agonist in which the amylin agonist and insulin are present in a ratio of about 1:20. Yet another related aspect concerns pharmaceutical compositions that include bolus blends of pramlintide and a short-acting insulin.

Another aspect that concerns commercial packages relates to those that include pharmaceutical formulations that contain an amylin agonist for parenteral administration to an insulin-using subject, wherein the package includes instructions for administering the amylin agonist in an amount and at a frequency to provide a basal plasma level of the amylin agonist over a 24-hour period that is equal to from between about 7% to about 15% of a basal level of an insulin to be administered to that subject.

Some embodiments of these aspects include articles of manufacture that include or further include at least one of the following: instructions for administering said amylin agonist one or more times per day in an amount and frequency to provide a mealtime bolus of said amylin agonist that is equal to from between about 2% to about 5% of a mealtime bolus amount of an insulin to be administered to the subject; the amylin agonist for basal administration is a long-acting amylin agonist; the amylin agonist for basal administration is pramlintide; the amylin agonist for basal administration is pramlintide, and the basal plasma level of pramlintide to be administered over a 24-hour period is equal to about 15% of the basal level of an insulin to be administered to said subject over the 24-hour period; the amylin agonist to be administered as a mealtime bolus is pramlintide, and the amount of pramlintide to be administered as a mealtime bolus is equal to about 5% of the amount of an insulin to be administered as a mealtime bolus to said subject.

BRIEF DESCRIPTION OF FIGURES

This application contains at least one figure executed in color. Copies of this application with color drawing(s) will be provided upon request and payment of the necessary fee. A brief summary of each of the figures is provided below.

DETAILED DESCRIPTION

Figure 1:
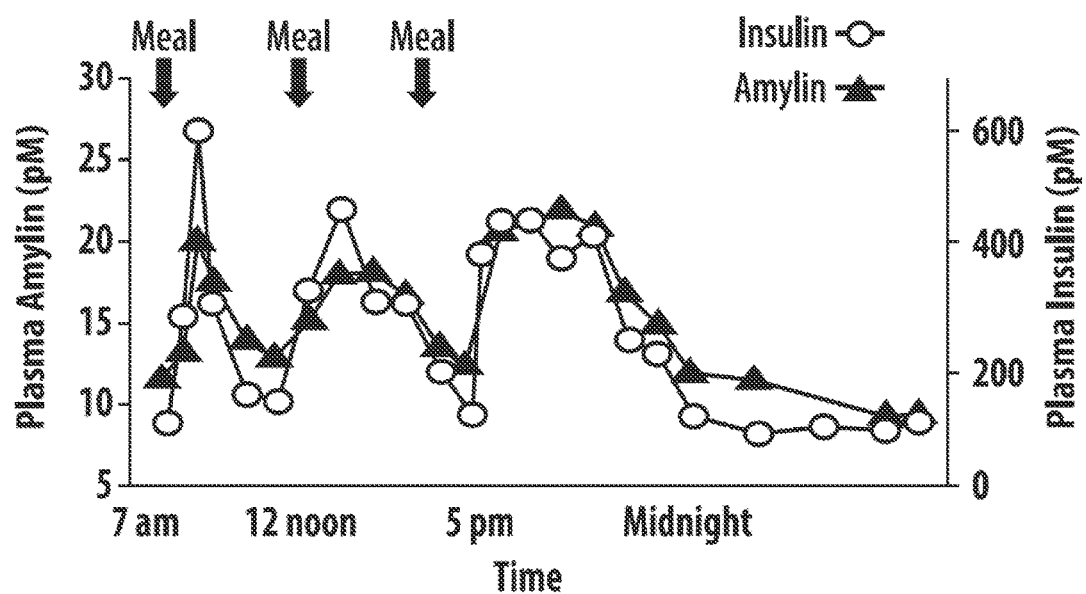
FIG. 1 is a profile of amylin and insulin secretion in healthy adults.

It is to be understood that the inventions are not limited to the particular devices, methodology, protocols, constructs, and reagents described herein and as such may vary. It is also to be understood that the terminology used herein is for the purpose of describing particular embodiments only, and is not intended to limit the scope of the present invention, which will be limited only by the appended claims. As used herein and in the appended claims, the singular forms "a," "an," and "the" include plural reference unless the context clearly indicates otherwise. Thus, for example, reference to an "amylin" is a reference to one or more such peptides and includes agonists and equivalents thereof now known or later developed. Unless defined otherwise, all technical and scientific terms used herein have the same meaning as commonly understood to one of ordinary skill in the art to which the inventions belong. Although any methods, devices, and materials similar or equivalent to those described herein can be used in the practice or testing of the invention, the preferred methods, devices and materials are now described. It is intended that reference to a range of numbers disclosed herein (for example 1 to 12) also incorporates reference to all related numbers within that range (for example, 1, 1.1, 2, 3, 3.9, 4, 5, 6, 6.5, 7, 8, 9.5, 10, 11 and 12) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner. The following terms have the following meanings when used herein.

In this document, the words "embodiment," "variant," "example," and similar expressions refer to a particular apparatus, process, or article of manufacture, and not necessarily to the same apparatus, process, or article of manufacture. Thus, "one embodiment" (or a similar expression) used in one place or context may refer to a particular apparatus, process, or article of manufacture; the same or a similar expression in a different place or context may refer to a different apparatus, process, or article of manufacture. The expression "alternative embodiment" and similar expressions and phrases may be used to indicate one of a number of different possible embodiments. The number of possible embodiments/variants/examples is not necessarily limited to two or any other quantity. Characterization of an item as "exemplary" means that the item is used as an example. Such characterization of an embodiment/variant/example does not necessarily mean that the embodiment/variant/example is a preferred one; the embodiment/variant/example may but need not be a currently preferred one. All embodiments/variants/examples are described for illustration purposes only.

The words "couple," "connect," and similar expressions do not necessarily import an immediate or direct connection, but include within their meaning connections through mediate elements.

"Causing to be displayed," "causing to be administered," "causing to be pumped," and analogous expressions refer to taking one or more actions that result in displaying, administering or pumping, and are not limited to display on an infusion pump or infusion pump system. A computer or a mobile device (such as a smart phone, tablet, Google Glass and other wearable devices), under control of program code, may cause to be displayed a picture and/or text, for example, to the user of the infusion pump or infusion pump system, and may be used in input data into a processor and/or provide instruction to the infusion pump or infusion pump system. Additionally, a server computer under control of program code may cause a web page or other information to be displayed by making the web page or other information available for access by a computer or mobile device, over a network, such as the Internet, which web page the client computer or mobile device may then display to a user of the computer or the mobile device.

The term "insulin" is intended to encompass wild-type insulin from any species including, but not limited to, porcine insulin, bovine insulin, and human insulin, including recombinantly-produced insulins. Native or wild-type insulin refers to insulin having an amino acid sequence corresponding to the amino acid sequence of insulin as found in nature. Polynucleotide and amino acid sequences encoding insulin from a number of different species are well known to those of ordinary skill in the art. For example, human insulin has a twenty-one amino acid A-chain and a thirty amino acid B-chain. Insulin can be natural (i.e., isolated from a natural source), biosynthetically, or synthetically produced. The term "insulin" is also intended to include any insulin derivative and/or insulin analog.

An "insulin analog" or "insulin derivative" is defined herein as protein having insulin activity and substantially the same amino acid sequence as human insulin but differing from human insulin by a modification relative to human insulin including one or more amino acid substitutions, deletions, inversions, or additions. Such compounds are well known in the art. See, e.g., PCT international patent application publication nos. WO 96/15804 and WO 03/053339; U.S. Pat. Nos. 3,528,960, 5,514,646, 5,618,913, 5,750,497, 6,011,007, 6,251,856; and EP patent nos. 254,516 and 280,534. An exemplary but non-exhaustive list of insulin analogs known to one skilled in the art includes insulin aspart, insulin lispro, insulin glargine, insulin detemir, and insulin glulisine. Furthermore, the term "insulin" herein also covers compounds which can be considered as being both an insulin derivative and an insulin analog. Examples of such compounds are described in the U.S. Pat. Nos. 5,750,497, and 6,011,007. A specific example of such a compound known to one skilled in the art is insulin detemir.

Various insulin analogs and/or derivatives are known to be "fast-acting" or "rapid-acting" insulin analogs. The terms "fast-acting" and "rapid-acting" are used interchangeably herein. A "rapid-acting insulin analog" produces a prandial glucose effect that (a) begins sooner after subcutaneous administration than human insulin, and/or (b) exhibits a shorter duration of action than human insulin after subcutaneous administration. Exemplary fast-acting insulin analogs include "monomeric insulin analogs" that are fast-acting because they are generally less prone to dimerization or self-association under physiological conditions. Monomeric insulin analogs are known in the art. See, e.g., U.S. Pat. No. 5,700,662, and European Patent No. 214 826. Insulin lispro is a rapid-acting, monomeric insulin analog in which the proline at position 28 of the wild-type insulin B-chain and the lysine at position 29 of the wild-type insulin B-chain have been switched. Accordingly, insulin lispro is known in the art by various designations including, but not limited to, $Lys^{B28}Pro^{B29}$-human insulin, LysB28ProB29-human insulin, and B28Lys, B29Pro human insulin.

Compositions of the invention, which in a non-limiting preferred embodiment are isolated or substantially pure, include the combinations of an insulin and an amylin agonist in any of the ratios described or referenced herein, or as may be calculated as described herein.

The term "amylin agonist" as used herein means an amylin, an amylin analog, an amylin derivative, and other compounds that mimics one or more effects (or activity) of an amylin in vitro or in vivo.

"Amylin" as used herein refers to a human peptide hormone of 37 amino acids referred to as amylin, which is co-secreted with insulin from the beta cells of the pancreas. Human amylin has a disulfide bridge between the two Cys residues at positions 2 and 7 and an amide group attached to the C-terminal amino acid residue via a peptide bond. The term also includes variants of amylin as present in, and in isolatable form, other mammalian species, for example, rodent amylin. With respect to a naturally occurring amylin compound, the term includes such a compound in an isolated, purified, or other form that is otherwise not found in nature.

An "agonist" of amylin refers to a compound that mimics one or more effects (or activity) of amylin in vitro or in vivo. The effects of amylin include the ability to directly or indirectly interact or bind with one or more receptors that are activated or deactivated by amylin, for example, the receptor binding assay and the soleus muscle assay described in Examples 2 and 3, respectively in WO 2004/037168. Preferred amylin agonists may also be compounds having at least 60, 65, 70, 75, 80, 85, 90, 95, or 99% amino acid sequence identity to human amylin and having amylin activity. Exemplary amylin agonists contemplated in the use of the invention include those described in U.S. Pat. Nos. 5,686,411, 6,114,304, and 6,410,511, which are herein incorporated by reference in their entirety.

"Non-amylin-based amylin agonists" are non-amylin-based agonists not based on amylin sequences or structures, i.e., compounds other than an amylin, an amylin analog, or an amylin derivative, that also mimics one or more effects (or activity) of amylin in vitro or in vivo. They include a calcitonin, which, as used herein, refers to the human peptide hormone calcitonin and non-human species variations of it, such as that of rat, salmon and eel (including aminosuberic eel calcitonin). "Non-amylin-based amylin agonists" are useful in the inventions described herein.

An "analog" or "analogue" or "agonist analog" of amylin refers to a compound that is similar in structure (e.g., derived from the primary amino acid sequence of amylin by substituting one or more natural or unnatural amino acids or peptidomimetics) to amylin and mimics an effect of amylin in vitro or in vivo.

The nomenclature of various amylin analogs useful in the present invention can be used to indicate both the peptide that the sequence is based on and the modifications made to any basic peptide amylin sequence, such as human amylin. An amino acid followed by a number or an amino acid preceded by a superscript number indicates that the named amino acid replaces the amino acid normally present at the amino acid position of the number/superscript number in the basic amino acid sequence. For example, "Arg18 Pro25 Pro 28-h-amylin" and "$^{18}$Arg$^{25,28}$Pro-h-amylin" refers to a peptide based on the sequence of "h-amylin" or "human-amylin" having the following substitutions: Arg replacing His at residue position 18, Pro replacing Ala at residue position 25, and Pro replacing Ser at residue position 28. The terms "des-Lys1-h-amylin" and "des-$^1$Lys-h-amylin" refers to a peptide based on the sequence of human amylin, with the first, or N-terminal, amino acid deleted. Amylin analogs useful according to the invention may also include fragments of amylin such as those described in EP 289287, the contents of which are herein incorporated by reference.

Amylin analogues also include amylin having insertions, deletions, and/or substitutions in at least one or more amino acid positions. The number of amino acid insertions, deletions, or substitutions may be at least 1, 2, 3, 4, 5, 6, or 10. Insertions or substitutions may be with other natural or unnatural amino acids, synthetic amino acids, peptidomimetics, or other chemical compounds. Exemplary compounds include, but are not limited to, pramlintide. Other compounds useful in the invention include des-Lys1-h-amylin, Pro28-h-amylin, Pro25 Pro28 Pro29-h-amylin, Arg18 Pro25 Pro28-h-amylin, Pro25 Val26 Pro 28 Pro29-h-amylin, and Arg18 Pro25 Pro 28-des-Lys1-h-amylin, which all show amylin activity in vivo in treated test animals, (e.g., provoking marked hyperlactemia followed by hyperglycemia).

A "derivative" of an amylin or amylin agonist or a non-amylin-based amylin agonist refers to an amylin or amylin agonist or a non-amylin-based amylin agonist which is chemically modified, e.g., by introducing a side chain in one or more positions of the amylin or amylin agonist or a non-amylin-based amylin agonist backbone or by oxidizing or reducing groups of the amino acid residues in the amylin or amylin agonist or a non-amylin-based amylin agonist or by converting a free carboxylic group to an ester group or to an amide group. Other derivatives are obtained by acylating a free amino group or a hydroxy group. Examples of amylin derivatives are described in the international patent application WO 2007/104789 and European Patent Application No. 07116067.5. Further examples of amylin derivatives are N-methylated amylin, such as the amylin peptide described in Yan et al., PNAS, vol. 103, no. 7, p. 2046-2051, 2006, where the amylin is N-methylated in positions 24 and 26.

Thus, an "amylin" includes an "amylin agonist", for example, and may be selected, for example, from the group consisting of human amylin, rat amylin, mouse amylin, pramlintide, etc. Other amylin agonists useful in the inventions are disclosed in U.S. Pat. No. 5,686,411 ("Amylin agonist peptides and uses therefor"), as noted above.

Also within the scope of the invention are compositions of the invention that include insulin and/or amylin (and/or agonists of either, including receptor agonists) that have been modified to improve their biopharmaceutical properties. In certain embodiments, the compounds of the invention are modified, for example, to provide increased stability, increased resistance to proteolytic inactivation, decreased to nonexistent immunogenicity, increased circulatory lives, including modified serum half-lives and modified therapeutic half-lives, and low toxicity. Modified forms of compounds of the invention include prodrug forms, representative examples of which are described elsewhere herein. Methods by which the compounds of the invention can be modified also include, for example, by PEGylation, by chemical derivitization, and by fusion or conjugation with peptides or lipids.

The term "treatment" or "treating" as used herein refers to the management and care of a patient having diabetes or hyperglycemia, or other condition for which amylin and/or insulin administration is indicated for the purpose of combating or alleviating symptoms and complications of those conditions. Treating includes administering compounds or compositions of the present invention to prevent the onset of symptoms or complications, alleviating the symptoms or complications, or eliminating the disease, condition, or disorder. The patient to be treated is a mammal, and preferably, a human being.

"Product" means any machine, article of manufacture, and/or composition of matter, unless expressly specified otherwise. "Process" means a process, algorithm, method, or the like, unless expressly specified otherwise. Any process includes one or more steps, and therefore all references to a "step" or "steps" of a process have an inherent antecedent basis in the mere description of a process, or in the mere recitation of the term "process" or a like term.

The term "invention" means the one or more inventions disclosed in this application.

The term "plurality" means two or more.

The term "represent" means (1) to serve to express, designate, stand for, or denote, as a word, symbol, or the like does; (2) to express or designate by some term, character, symbol, or the like; (3) to portray or depict or present the likeness of, as a picture does; or (4) to serve as a sign or symbol of. "Represent" and like terms are not exclusive, unless expressly specified otherwise. For example, the term "represents" does not mean "represents only".

"Determining" and grammatical variants thereof, including "determine," is used in an extremely broad sense, and encompasses a wide variety of actions and therefore "determining" can include calculating, computing, processing, deriving, investigating, looking up (e.g., looking up in a table, a database or another data structure), rendering into electronic format or digital representation, ascertaining, and the like. Also, "determining" can include receiving (e.g., receiving information), accessing (e.g., accessing data in a memory), and the like. Also, "determining" can include resolving, selecting, choosing, establishing, and the like.

"Determining" does not imply certainty or absolute precision, and therefore "determining" can include estimating, extrapolating, predicting, solving, deducing, supposing, averaging, and the like. "Determining" also does not imply that mathematical processing must be performed, that numerical methods must be used, or that an algorithm or any particular device must be used.

"Determining" typically includes performing one or more calculations. Calculating may include computing, processing, and/or deriving. A computing device may perform calculating. For example, calculating a thing may include applying an algorithm to data by a computer processor and generating the thing as an output of the processor.

"Determining" may also include "referencing", which should be understood to include making one or more references, e.g., to a thing. Referencing may include querying, accessing, selecting, choosing, reading, and/or looking-up. A computing device may perform the act of referencing. For example, referencing a thing may include reading a memory location in which the thing is stored by a processor.

"Determining" may also include "receiving". For example, receiving a thing may include taking in the thing. In some embodiments, receiving may include acts performed to take in a thing, such as operating a network interface through which the thing is taken in. In some embodiments, receiving may be performed without acts performed to take in the thing, such as in a direct memory write or a hard wired circuit. Receiving a thing may include receiving a thing from a remote source that may have calculated the thing.

The words "couple," "connect," and similar expressions with their inflectional morphemes do not necessarily import an immediate or direct connection, but include within their meaning connections through other elements.

"Computing device," "computer," and analogous expressions refer to one or devices including at least a tangible computing element. Examples of a tangible computing element include but are not limited to a microprocessor, application specific integrated circuit, programmable gate array, and the like. Examples of a computing device include but are not limited to a mobile computing device such as a smart phone or tablet computer, a wearable computing device (e.g., Google® Glass), a laptop computer, a desktop computer, or any other form of computing device. A computing device preferably includes or accesses storage for instructions used to perform steps such as those discussed in this document and data such as images on which those steps may be performed.

"Computer-implemented" and analogous expressions refer to technology implemented using, by, or on one or more computing devices.

"Causing to be displayed" and analogous expressions refer to taking one or more actions that result in displaying. A computing device, under control of program code, may cause to be displayed a picture and/or text, for example, to the user of the computing device. For example, a computing device may cause pictures and/or text to be displayed directly to a user. For another example, a server computer under control of program code may cause a web page or other information to be displayed by making the web page or other information available for access by a client computer or mobile device, over a network, such as the Internet, which web page the client computer or mobile device may then display to a user of the computer or the mobile device.

Other and further explicit and implicit definitions and clarifications of definitions may be found throughout this document.

As noted above, the only amylin agonist on the market, pramlintide, has not met patient needs and is not widely used. Also, as previously noted, while dual administration of a therapeutically effective amount of pramlintide and a therapeutically effective amount of an insulin was patented in 1997, almost 20 years ago, no such product or combination therapy has been marketed or developed. It is further noted that a significant barrier to restoring normal blood glucose levels in T1D is the risk of serious hypoglycemia, which has been documented as among the largest direct medical costs of T1D. Healthy people do not experience true hypoglycemia, because falling blood glucose stimulates a glucagon counter-regulatory response (GCR): when blood glucose falls below normal levels, pancreatic alpha-cells secrete glucagon which stimulates the liver to release glucose into circulation. In patients with T1D this GCR mechanism is lost, with the result that falling blood glucose does not stimulate liver-produced glucose. Consequently, it is very risky for T1D patients to use enough insulin to bring blood glucose into the normal range, because they no longer have this GCR protective mechanism.

Normal alpha-cell GCR is controlled by beta-cells via two mechanisms: (1) a beta-cell signal that suppresses alpha-cell secretion of glucagon when blood glucose is at normal levels or elevated; and (2) a "switch-off trigger" that cancels the beta-cell suppression signal when blood glucose falls into the hypoglycemic range. The beta-cell hormone amylin satisfies both of these requirements: (1) at normal or elevated blood glucose levels, amylin suppresses glucagon secretions via the autonomic nervous system; and (2) during hypoglycemia this amylin signal is turned off by the autonomic nervous system to permit unrestrained glucagon secretion. In other words, amylin will suppress alpha-cell secretion of glucagon, except when plasma glucose declines to hypoglycemic levels. We believe that the amylin deficiency caused by beta-cell destruction in T1D is the most important underlying cause of defective GCR.

As noted above, there remains a need in the art for new devices, methods and therapeutics useful in treating patients having diseases, disorders and conditions that may be treated with insulin and/or amylin, or their agonists, including T1D and T2D. There is a particular need for new devices and therapeutics that span the entire spectrum of diseases, disorders and conditions associated with amylin deficiency, particularly those that are also benefited by treatment with insulin. Such devices, methods and therapeutics are described and claimed herein.

As noted, administration of an amylin agonist, e.g., an analogue (e.g., pramlintide) in proportion to an insulin as described herein will improve and stabilize or normalize glucose levels, distribution, and metabolism. In still another aspect, administration of an amylin analogue in proportion to insulin as described herein will improve the glucagon counter-regulatory response. The term "stabilize" has its generally recognized meaning in the art, i.e. to avoid fluctuations. Stabilization may be seen by a reduction in the percentage of time that plasma glucose is in hypoglycemic or hyperglycemic ranges that are considered unhealthy or undesirable. A patient (or patient population) receiving the inventive therapy would have a reduced rate, or reduced incidence, of hypo- and/or hyperglycemia and/or other adverse side effects of insulin-only therapy, or insulin cotherapy, for example, with pramlintide as it is prescribed in the package insert. Normalized glucose levels may be evaluated, for example, by average HbA1c measurements, or the like. Normalized glucose distribution refers to glucose amounts typically distributed in or levels seen at relevant time periods in blood, muscle and liver, for example.

Reference will be made in detail to several aspects of the invention that are illustrated in the accompanying Figures. The drawings in the Figures are in a simplified form, may not be precisely to scale, and may omit apparatus elements, method steps, and other features that may be added to the described systems and methods, and dosing relationships, and may or may not certain optional elements and steps.

In various aspects, the inventions includes (1) methods of calculating the dose of an amylin agonist based on two components, whereby the first portion is determined by a patient's basal dosing of insulin and the second portion is determined by a patient's bolus dosing of insulin; (2) methods of treating diabetes and other glucose-handling disorders characterized at least in part by hyperglycemia, using a dual chamber hormone pump programmed to calculate the proper infusion rate of an amylin agonist based on two components, whereby the first portion is determined by a patient's basal infusion rate of insulin and the second portion is determined by a patient's bolus infusions; (3) formulations combining insulin and an amylin agonist in distinct and different ratios based upon whether the formulation is for basal or for bolus dosing, with the basal ratio being higher than the bolus ratio. Patch pumps may also be used, as noted.

The invention includes a programmable multiple drug chamber medical infusion pump or infusion pump system, or by patch pumps, wherein (a) the processor is programmed to calculate a basal delivery rate for an amylin agonist based on a predetermined basal dosing ratio of amylin agonist to basal insulin, (b) the processor is programmed to calculate a bolus delivery rate for said amylin agonist (including, e.g., an amylin analogue such as pramlintide) based on a predetermined bolus dosing ratio of amylin agonist to bolus insulin, and (c) the processor uses these calculations to cause the pump mechanism to deliver said amylin agonist in dosing amounts and at delivery rates substantially equal to the calculated basal and bolus amounts and rates over programmed periods of time.

Also within the invention is a method for treating an insulin-using subject with an amylin agonist, comprising basal and bolus amylin agonist components which are determined by two different dosing ratios to the insulin basal and bolus components, with the basal ratio being higher than the bolus ratio.

As noted in the Background, at least two issues with the amylin agonist pramlintide have discouraged patients and caregivers from its use. The first is multiple injections. Many patients who respond well to the drug eventually grow tired of pre-meal injections, and many patients who should try pramlintide are put off by the idea of three more daily shots. The second is adverse events.

With respect to multiple injections, two approaches are seen to solving this problem:

Blend pramlintide with insulin: A co-formulation would satisfy patients continuing to use insulin syringes or pens, and it could be infused by currently available insulin pumps.

Develop a dual hormone pump, or patch pumps: If pumpers could easily add pramlintide to their infusion sets, the multiple injection objection may be reduced or disappear.

These approaches to the injection objection, however, would not address the low therapeutic index problem, which is based on the current delivery regimen of pre-meal boluses. Indeed, to date no one has developed an amylin agonist/insulin blend or a dual amylin agonist/insulin pump.

The basic concept behind FDA-approved pramlintide dosing appears to have been to provide mealtime boluses of an endogenous amylin similar to those that are supplied by healthy pancreatic beta-cells. Discussions of amylin endocrinology always state that amylin is co-secreted with insulin from beta-cells, and a commonly referenced 24-hour hormone profile in healthy adults appears to show that amylin plasma profiles closely parallel those of insulin. FIG. 1 is copied directly from pramlintide's FDA-approved Package Insert, and it is also presented in a recent journal review of pramlintide therapy.

Thus, the basic concept behind recommended pramlintide dosing is to mimic the mealtime boluses of endogenous amylin that are supplied by healthy pancreatic beta-cells. To this end, and to simplify patient use, pramlintide is supplied in prefilled pens that dispense selections of fixed doses. They are SymlinPen 60, which is available in 15 µg, 30 µg, 45 µg, and 60 µg doses, and SymlinPen 120, which is available in 60 µg and 120 µg doses.

Following are pramlintide Package Insert instructions for T1D patients:

In patients with type 1 diabetes, pramlintide should be initiated at a dose of 15 µg and titrated at 15 µg increments to a maintenance dose of 30 µg or 60 µg as tolerated:

Initiate pramlintide at a starting dose of 15 µg subcutaneously, immediately prior to major meals;

Reduce pre-prandial, rapid-acting or short-acting insulin dosages, including fixed-mix insulins (e.g., 70/30) by 50%;

Monitor blood glucose frequently, including pre- and post-meals and at bedtime;

Increase the pramlintide dose to the next increment (30 µg, 45 µg, or 60 µg) when no clinically significant nausea has occurred for at least 3 days. If significant nausea persists at the 45 or 60 µg dose level, the pramlintide dose should be decreased to 30 µg. If the 30 µg dose is not tolerated, discontinuation of pramlintide therapy should be considered;

Adjust insulin doses to optimize glycemic control once the target dose of pramlintide is achieved and nausea (if experienced) has subsided.

The result of this protocol is that patient-specific doses of pramlintide are determined by a patient's tolerance to its dose limiting effect, which is nausea. The optimal dose is not determined by (1) its effect on glucose control, (2) the pre-pramlintide insulin dosing which was optimized by the patient, nor (3) the individual characteristics of the patient, e.g., body weight.

Figure 2:
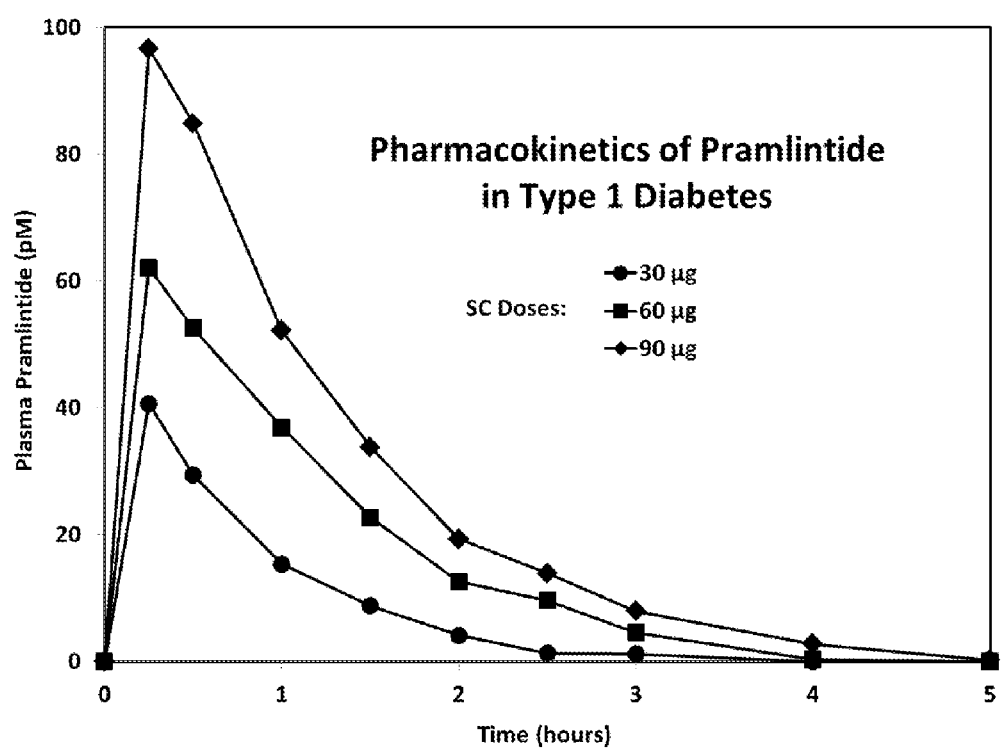
FIG. 2 shows the post-injection levels of plasma pramlintide for three subcutaneous doses (30 µg, 60 µg and 90 µg).
Figure 3:
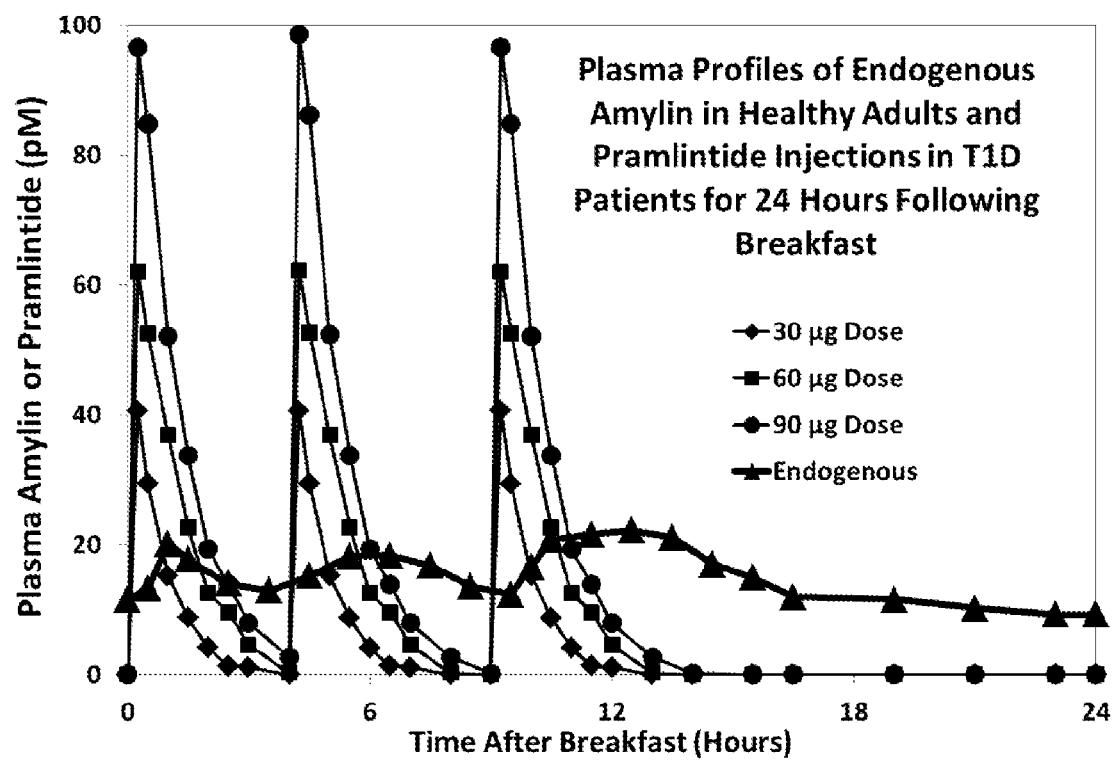
FIG. 3 shows plasma levels of the three subcutaneous doses of pramlintide from FIG. 2 superimposed on the plasma amylin profile in healthy adults FIG. 1.

How well do the recommended mealtime injections of pramlintide mimic the healthy plasma amylin profile? FIG. 2 shows the post-injection levels of plasma pramlintide for three subcutaneous doses, and it indicates that pramlintide has largely cleared plasma within three hours, i.e. usually before the next meal. In the case of three meals per day, these doses would result in three large boluses of pramlintide that spike well above the levels of plasma amylin measured in healthy adults. FIG. 3 superimposes plasma levels of the three subcutaneous doses of pramlintide (FIG. 2) on the plasma amylin profile in healthy adults (FIG. 1).

These data demonstrate that T1D patients experience supra-physiological (or pharmacological) plasma levels of pramlintide three times daily at these doses, and these pharmacological spikes can explain the nausea associated with the drug. These spikes are also likely to disrupt the rate at which oral glucose can counteract hypoglycemia, thereby causing hypoglycemia stickiness.

Figure 4:
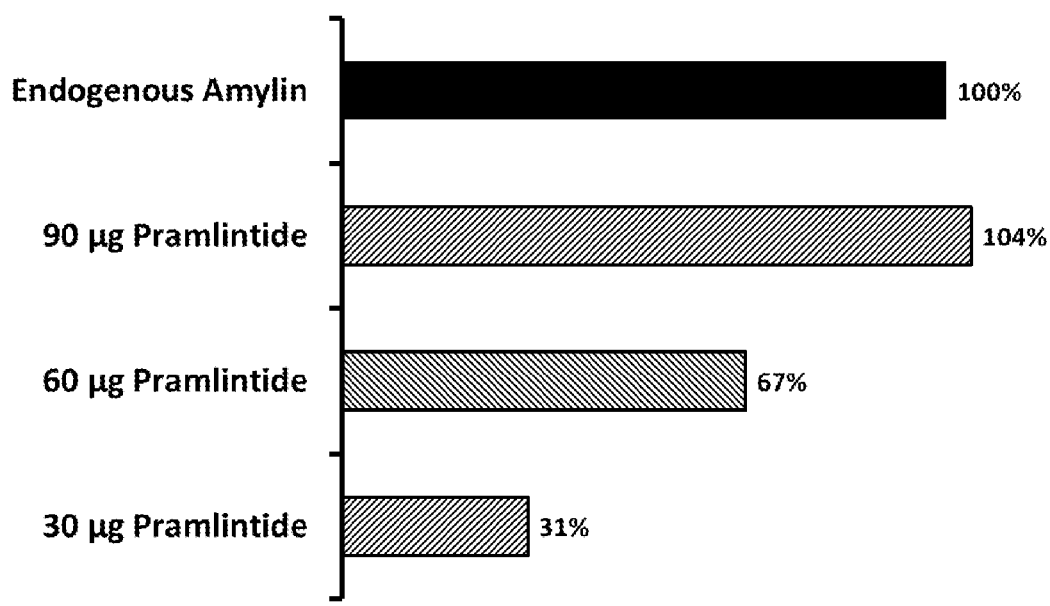
FIG. 4 shows the AUC of endogenous amylin at 100%, and the relative AUCs of the three 30 µg, 60 µg and 90 µg pramlintide doses, measured as percentages of the area under the 24-hour plasma profile of endogenous amylin in health adults.

From an efficacy standpoint, the dose limiting effect of nausea caused by pramlintide plasma spikes reduces daily drug exposure below healthy plasma amylin exposure levels. Daily exposure to endogenous hormone and infused drug can be measured by calculating the areas under the curves (AUCs) in FIG. 3. Setting the AUC of endogenous amylin at 100%, the relative AUCs of the three pramlintide doses are shown in FIG. 4.

These AUCs indicate relative exposure to the amylin analog over a 24-hour period, and they demonstrate that only the 90 μg dose achieves the healthy, 24-hour physiological exposure in healthy adults. However, the dose titration instructions in the package insert do not include this highest dose for T1D, nor can it be dialed into either SymlinPen; as a result, most T1D patients are receiving sub-physiological exposure to pramlintide. This deficiency explains why many patients do not benefit from the full glucose control efficacy of pramlintide.

The above discoveries and analyses indicate that mealtime injections cause supra-physiological spikes in plasma pramlintide levels, which can cause nausea. They also support the idea that the lack of a basal infusion of pramlintide reduces the 24-hour exposure below the amount observed in healthy adults, which can cause a blunting of pramlintide's efficacy to improve insulin replacement therapy by lowering and stabilizing plasma glucose levels and glucose metabolism, and to reestablish or restore GCR protection against hypoglycemia.

We have determined, furthermore, how to alter pramlintide dosing to address both spiking and suboptimal exposure. One approach is to use a medical infusion pump or infusion pump system to deliver basal pramlintide dosing. In another preferred approach pramlintide is infused continuously throughout the day with appropriate boluses at mealtime. Patients could use a pump to deliver the basal component and a SymlinPen to deliver the mealtime boluses. Assuming the process of pumping pramlintide did not change its efficacy and safety, this approach would be expected to achieve much more rapid regulatory approval than a new longer-acting molecule, such as that proposed in U.S. Pat. No. 8,486,890.

Use of a long-acting amylin agonist for basal exposure was proposed in the 8,486,890 patent, which indicates that it would be useful to provide derivatives that have the activities of native human amylin, as well as derivatives which have a protracted pharmacokinetic profile, and show enhanced solubility and/or stability over native human amylin. To address this, the patent discloses amylin molecules that incorporate a lysine residue or cysteine residue linked to an albumin binding residue or a polyethylene glycol polymer. No data about the plasma half-lives of the proposed long acting amylin analogs are presented.

Neither of these solutions, however, would obviate the need for additional injections, which is an important obstacle to patient acceptance of amylin replacement therapy. Also, the insulin pump solution would require patients to wear two pumps if they also wished to pump insulin.

Beyond the problem of additional injections and pumps, these two approaches also do not address the goal of optimizing the daily plasma profile of pramlintide for individual patients. In the case of insulin T1D patients are taught to customize their dosing to their own needs, based on their daily exercise and eating patterns, as well as their bodies' individual responses to insulin therapy. Just as it is not possible to specify one simple regimen for all insulin users, it is not reasonable to expect that amylin replacement therapy can avoid individual optimization.

What is needed is an amylin agonist dosing regimen that accomplishes two objectives: (1) correctly mimic the physiological daily plasma profiles and exposure of both pancreatic hormones, insulin and amylin; and (2) provide a simple algorithm for optimizing amylin agonist dosing based on individual patient needs.

As described above, since amylin's discovery in the late 1980s it has been widely believed that endogenous insulin and amylin are secreted in relatively constant ratios and therefore appear in the plasma in similar profiles, as shown in FIG. 1 which is taken from the FDA-approved package insert for pramlintide. In FIG. 1, however, the amylin scale has been truncated at a concentration of 5 pM. This gives the appearance that insulin and amylin have virtually identical 24-hour profiles. Presumably the vertical axis was truncated at 5 pM rather than 0 pM because the authors knew that insulin and amylin are packaged together and co-secreted from beta-cells, which might be expected to result in alignment of plasma hormone profiles.

Figure 5:
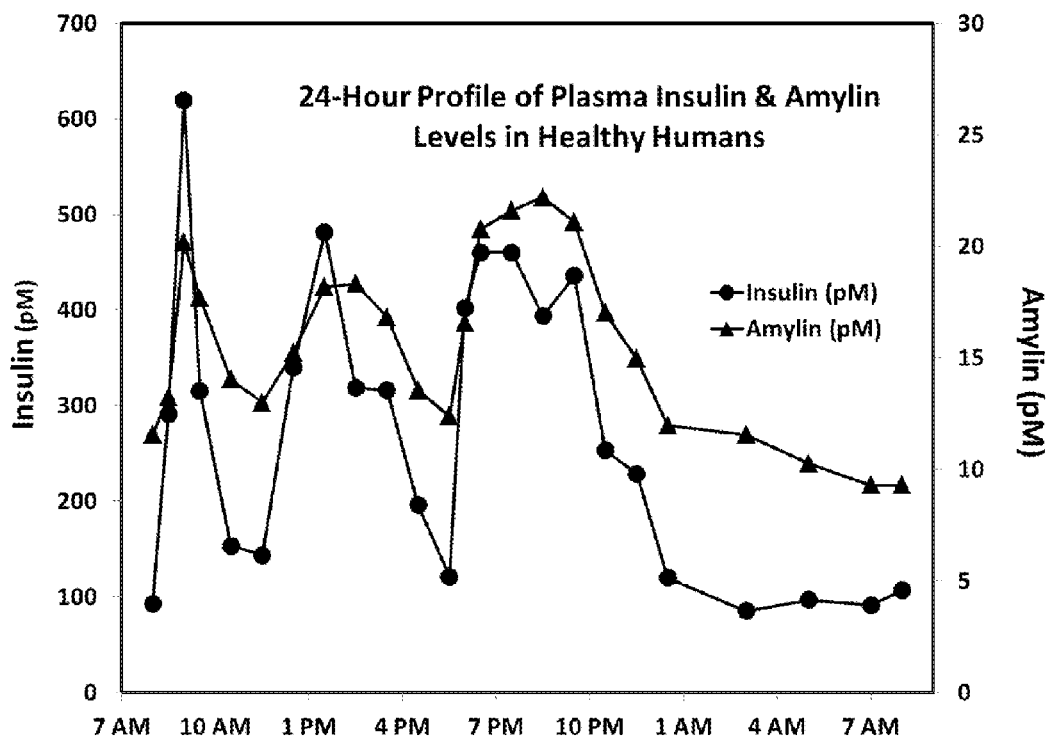
FIG. 5 shows 24-hour profiles for insulin and amylin in healthy adult humans.

When the FIG. 1 chart is adjusted so that the amylin axis begins at zero pM as in FIG. 5, the shapes of the amylin and insulin profiles are different in at least one very important way: the basal plasma level of amylin represents a bigger proportion of total plasma amylin than basal insulin is of total insulin.

Figure 6:
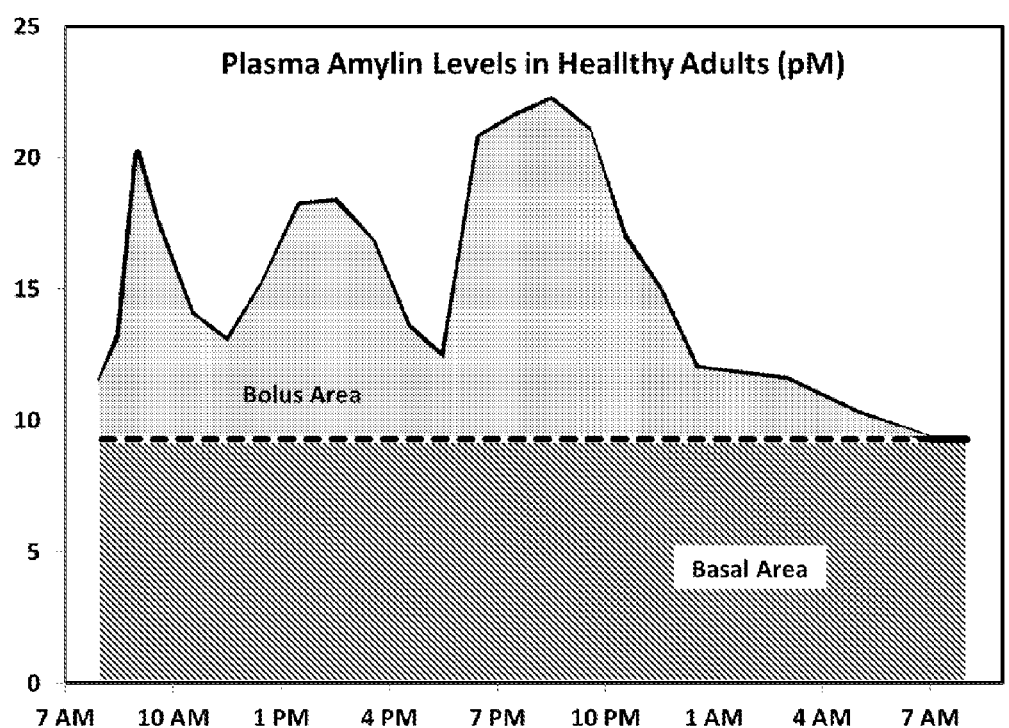
FIG. 6 shows plasma amylin levels in healthy adults (pM), divided into basal and bolus areas.
Figure 7:
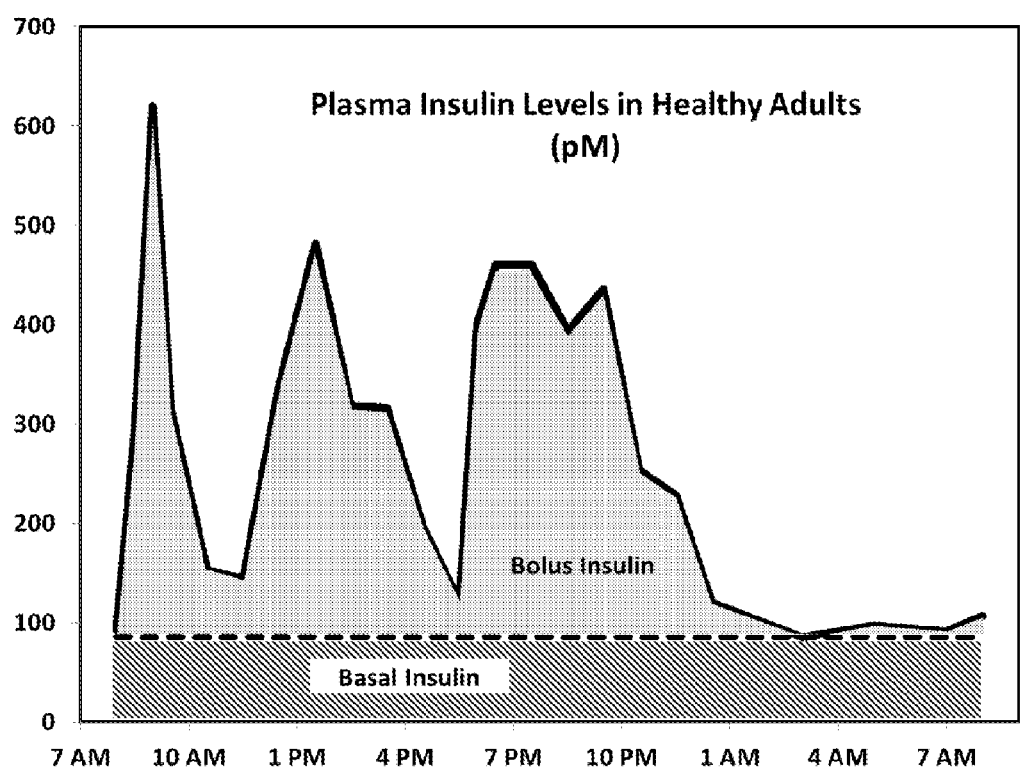
FIG. 7 shows plasma insulin levels in healthy adults (pM), divided into basal and bolus areas.

This difference in bolus/basal ratios was quantified by estimating the AUCs of the basal and bolus components, which would reflect the 24-hour hormone exposures attributable to these components. FIG. 6 and FIG. 7 show this basal/bolus allocation for amylin and insulin when the lowest observed levels of endogenous hormone are used as the upper boundary of the basal area.

Comparing AUCs results in the discovery that there is a striking difference between hormones with respect to the importance of bolus exposure compared to basal exposure, as summarized in Table 1. Measured as a ratio of bolus-to-basal exposure, the insulin bolus component is about three times as important as that of amylin. Measured as percentages of total daily hormone exposures, the "pancreatic insulin pump" secretes about twice as much insulin during mealtime boluses compared to basal, whereas the "pancreatic amylin pump" is set to the reverse ratio. See the example in Table 1.

TABLE 1

|  | | Based upon AUCs: | |
|---|---|---|---|
|  | Basal Level | Bolus/Basal Ratio | Basal as % Total |
| Insulin | 85.2 pM | 1.9 | 35% |
| Amylin | 9.3 pM | 0.6 | 62% |

Note that these calculations are based upon the specific clinical study shown in FIG. 5, and so the quantities presented here are used to illustrate the difference between insulin and amylin plasma levels. In other words, amongst other things, we have discovered that insulin is primarily a mealtime bolus hormone, whereas amylin is primarily a background basal hormone. This is demonstrated by plotting the insulin and amylin profiles on the same 0-700 pM scale, as shown in FIG. 8.

It is noted with regard to Table 1 that both the plasma insulin and amylin were measured with immunometric assays that are normally highly specific but are subject to cross reactions with other analytes that contain both binding sites. The same assay for plasma amylin was used to generate FIG. 1-D, which shows T1D patients averaging 1.6 pM plasma amylin even though they are presumed to have no beta-cell function. Either this is background amylin expression which been reported in non-beta-cell tissues, or it is nonspecific background noise in the amylin assay. In either case the basal amylin level in the above figures should therefore be reduced by about 17%. The same adjustment should also be made for any background insulin plasma levels. However, the insulin data is not available, so for this discussion the unadjusted plasma amylin basal level of 9.3 pM will be used in this example.

Figure 8:
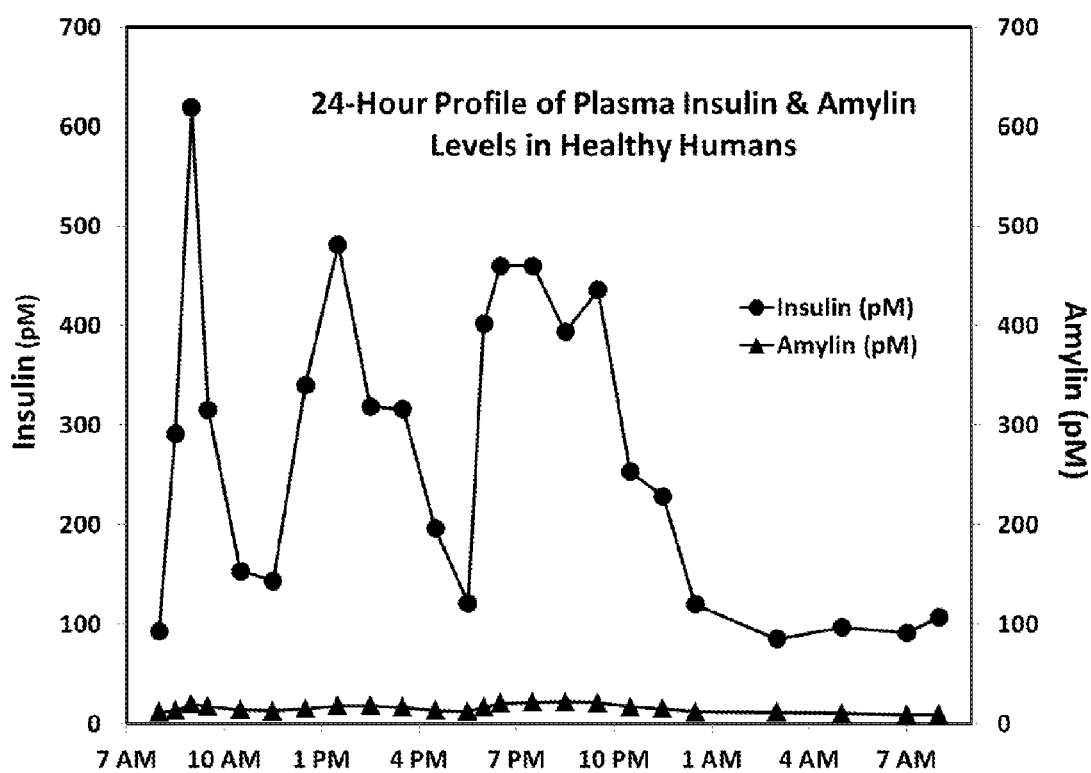
FIG. 8 shows a 24-hour profile of plasma insulin and amylin levels in healthy adults (pM).

One discovery from FIG. 8 is that amylin is a much more potent, neuroendocrine hormone than insulin, which operates primarily on peripheral tissues, i.e. muscle and fat. Amylin exerts its effects mainly through receptors in the brain, and its plasma levels are at much lower concentrations (less than 5% of insulin levels). Excursions outside of that physiological range may be deleterious for efficacy and explanatory, at least in part, for side effects.

Since the purpose of hormone replacement therapy is, in general, to mimic healthy endogenous secretion and plasma levels, subcutaneous dosing of hormone agonists in such a situation should be designed to achieve these differences in bolus/basal ratios. Since patients with diabetes, particularly T1D, adjust their daily insulin dosing to reflect exercise and eating patterns, a better way to accomplish this is to determine amylin agonist doses based on its healthy physiologic relationship to insulin. In this manner, patients would have a simple way to decide how much of an amylin agonist, e.g., pramlintide, to take based upon their individual insulin doses.

The following calculations are presented as an example of how appropriate amylin agonist doses can be determined. This insulin-dependent dosing can be achieved by calculating two separate components of pramlintide dosing: (1) the weight ratio of the daily basal component of amylin-to-insulin; and (2) the weight ratio of the daily bolus component of amylin-to-insulin. Table 2 shows this calculation: column two shows the calculated molar AUCs for endogenous insulin and amylin; column four shows endogenous gram AUCs after correcting for molecular weight differences; and column six shows exogenous gram AUCs after correcting for bioavailability of subcutaneous (SC) injections.

These calculations indicate that, to mimic healthy endogenous hormone levels, basal SC infusions of insulin should be accompanied by about 15% pramlintide by weight to insulin, and bolus SC injections of insulin should be accompanied by about 5% pramlintide by weight to insulin. In the example above clearance rates for insulin, amylin, and pramlintide are assumed to be approximately equal. For use in a dual hormone pump, or by patch pumps, the most likely choice of would be from among the rapid-acting varieties, e.g., APIDRA with an SC half-life of 42 minutes compared to the SC half-life of 48 minutes for SYMLIN. Note that this example calculation does not take into account the difference in clearance rates between pramlintide and the various kinds of insulin used to treat T1D. Accordingly, actual dosing ratios should be determined by taking into account the specific pharmacokinetics of the amylins and the insulins being used. Actual dosing ratios may also be adjusted as needed and appropriate by taking into account the specific pharmacodynamics of the amylins and the insulins being used.

Because insulin is traditionally dosed in Units rather than μg, it is more useful to express these ratios as μg of pramlintide per Unit of insulin as shown in Table 3.

TABLE 3

Example:
Calculation of Exogenous Pramlintide
Doses as Ratios to Insulin Doses

| | |
|---|---|
| Units per gram insulin: | 26,000 |
| Grams per 10 Units insulin: | 0.0000384615 |
| μg per 10 Units insulin: | 38.5 |
| Basal pramlintide μg/U insulin: | 5.7 |
| Bolus pramlintide μg/U insulin: | 1.9 |

To illustrate how these dose ratios would be used: Suppose a T1D patient is pumping 30 Units of insulin daily, 50% of which is basal. Applying the above dose ratios, an appropriate daily amount of pramlintide would require 15×5.7=85.5 μg for the basal insulin, and 15×1.9=28.5 μg for the insulin boluses. The indicated daily dose of pramlintide would thus be 85.5+28.5=114.0 μg. Using available SymlinPens, this daily dose could be achieved with three equal mealtime doses of about 40 μg, which is close to the 45 μg setting on the SymlinPen 60. Thus, the total daily pramlintide dose calculated this way from the insulin doses is within the range that was found to be safe and effective during pramlintide clinical studies.

However, three such equal bolus doses of pramlintide would cause the nausea and efficacy problems discussed

TABLE 2

Calculation of Dosing Ratios Based on Endogenous Hormone Ratios

| | In Vivo | | | | Ex Vivo |
|---|---|---|---|---|---|
| | AUC pM × 24 hr | Molecular Weight | AUC μg/L × 24 hr | Bio-availability | AUC μg/L × 24 hr |
| Basal Amylin | 222.79 | 3949 | 879.82 | 35% | 2513.76 |
| Basal Insulin | 2045.34 | 5808 | 11879.36 | 70% | 16970.52 |
| Basal Amylin/Insulin Ratio | 10.9% | | 7.4% | | 14.8% |
| Bolus Amylin | 135.19 | 3949 | 533.88 | 35% | 1525.37 |
| Bolus Insulin | 3813.31 | 5808 | 22147.72 | 70% | 31639.60 |
| Bolus Amylin/Insulin Ratio | 3.5% | | 2.4% | | 4.8% |

Note:
This calculation assumes equal clearance rates for subcutaneous delivery of insulin, amylin, and pramlintide.

above. Instead, based on the concept of basal/bolus dosing, pramlintide should be administered as follows:
  85.5 µg should be infused as a continuous basal level over 24 hours, i.e. at about 3.6 µg per hour.
  28.5 µg should be injected with the three insulin boluses, i.e. as 9.5 µg bolus doses at mealtime.

By administering pramlintide in this daily pattern of doses, for example, efficacy can be maximized without triggering nausea. The most practical, patient-friendly way to achieve this linkage between insulin and amylin agonist dosing would be by using a dual- or other multiple-chamber, independently programmable hormone pump, or by separately programmable patch pumps. Suitable multiple-chamber infusion pump system systems are described, for example, in U.S. Patent Application Publication No. 20130055816 ("Multi-Reservoir Infusion pump system Systems and Methods"). Such devices are capable of reliably delivering two or more therapeutic substances from a single device in an efficient manner for accurate treatment of medical conditions requiring multiple medicaments, such as an amylin agonist and an insulin. Other programmable pumps are described in other documents including, for example, in U.S. patent application publication no. 20130131630 ("Programmable Insulin Pump"). Suitable patch pumps are described above.

In a dual-chamber pump or in two patch pumps, for example, the amylin agonist (e.g., pramlintide) compartment would be programmed to infuse drug at rates calculated by the rates of infusion of insulin. In the quantitative example here:
  Basal: When the basal rate for insulin infusion is programmed into the pump, this would automatically determine the basal rate for pramlintide at 5.7 µg per Unit insulin.
  Bolus: When a bolus of insulin is triggered by the patient, this would automatically add a bolus of pramlintide equal to 1.9 µg per Unit insulin.

Note that these infusion rates for pramlintide in this Example are based on the data in FIG. 1, which is a single study of healthy patients. The dosing ratios calculated above for basal and bolus amylin agonist therapy are from one, relatively small study of insulin and amylin plasma levels in six healthy adults. These rates may differ among patients depending upon their individual needs.

There are various means to provide other, more refined dosing parameters. It is not unusual for studies of hormone levels to show significant standard deviations around the mean values, as illustrated in FIG. 1D. Consequently, efforts aimed at further refining these ratios may examine profiles in a larger sample of healthy individuals. During such evaluations other parameters to be evaluated for healthy individuals include, for example:
  Body mass index: More obese individuals tend to be insulin resistant, which could affect the amylin/insulin ratios.
  Age: Younger people, particularly growing adolescents, may display different ratios from older people.
  Exercise and diet: The amylin/insulin ratios may vary in the same individuals depending upon what they eat and whether meals are followed by vigorous exercise.
  Glucagon secretion: Given the role amylin plays in suppressing postprandial glucagon secretion, it would be useful to determine if differences in pre-prandial glucagon secretion are reflected in individual patient amylin/insulin ratios.

As clinical experience using the amylin/insulin ratios accumulates, other parameters may be found to be useful for optimizing individual patient experiences. Of course, as patients become more familiar with dual hormone therapy, they may want to adjust the ratios to suit their own metabolism. This may be taken into account not only by injections, but in programming the infusion pumps and/or infusion pump systems useful in the invention.

An alternative approach is to formulate insulin/amylin agonist blends depending upon whether the combination was to be used for bolus or basal dosing. In the quantitative example here:
  Basal: Long acting insulins (e.g., LANTUS) would be blended at 5.7 µg amylin agonist per Unit insulin.
  Bolus: Rapid acting insulins (e.g., APIDRA) would be blended at 1.9 µg amylin agonist per Unit insulin.

For these blends to work properly, the pharmacokinetics of the amylin agonist would preferably parallel those of the insulins. The bolus formulations would be compatible with the rapid onset and clearance of pramlintide (or another amylin or amylin agonist), but the basal formulations would preferably include either a different amylin agonist with pharmacokinetics similar to the long acting insulin, or a sustained release mechanism for the pramlintide component.

Another alternative is to administer pramlintide differently for the basal and bolus components using a combination of injections and a pump. In this quantitative example:
  Basal: Pramlintide would be infused by a pump set to deliver 5.7 µg per Unit basal insulin, which could be administered as an injection of long acting insulin or could be delivered by a separate pump.
  Bolus: Pramlintide would be injected at mealtimes via SymlinPen or pump in doses set at 1.9 µg per Unit bolus insulin, which could be administered as an injection of short acting insulin or could be delivered by a separate pump.

The invention includes, of course, any other way to administer an amylin agonist with insulin so that appropriate basal and bolus dose ratios are administered and, preferably, maintained.

In one aspect, the invention includes devices for dual administration of an insulin and an amylin agonist in different bolus and basal administration ratios to subjects in need of thereof. Bolus amylin agonist/insulin administration ratios and basal amylin agonist/insulin administration ratios are described herein. Ratios may adjusted, or otherwise calculated or determined, as described herein.

In various embodiments, the invention includes a programmable multiple drug chamber medical infusion pump or infusion pump system wherein (a) the processor is programmed to calculate a basal amount and delivery rate for an amylin agonist based on a predetermined basal dosing ratio of amylin agonist to basal insulin, or from a range of ratios, (b) the processor is programmed to calculate a bolus amount and delivery rate for said amylin agonist based on a predetermined bolus dosing ratio of amylin agonist to bolus insulin, or from a range of ratios, and (c) the processor uses these calculations to cause the pump mechanism(s) to deliver said amylin agonist in dosing amounts and at delivery rates substantially equal to the calculated basal and bolus amounts and rates over programmed periods of time. Embodiments may be directed to infusion devices or systems and methods of using these devices or systems for dispensing an insulin and an amylin agonist in particular ratios in a controllable and reliable manner. In some cases, embodiments include portable infusion pump or infusion pump systems and methods of using such pumps for infusing, for example, multiple blood glucose-modulating amylin agonist pharmaceutical materials and insulin pharmaceutical materials, to a patient.

The systems described herein may also include continuous glucose monitoring (CGM). With CGM, people with diabetes get a more complete picture of their glucose levels, which can lead to better treatment decisions and better glucose control. CGM measures glucose levels in real time throughout the day and night. CGM provides the direction glucose levels are going; early notification of oncoming lows and highs; alerts for lows or highs while the patient is sleeping; and insights into how food, physical activity, medication, and illness impact glucose levels. A CGM system generally comprises a glucose sensor inserted under or on the skin that measures glucose levels. a transmitter that sends the glucose information from the sensor to a monitor, an external monitor (which may be built into an insulin pump or a stand-alone device) that displays glucose levels on a screen and notifies the user if it detects that glucose is reaching a high or low limit. See, e.g., Thabit and Hovorka, "Closed-loop Insulin Delivery in Type 1 Diabetes." *Endocrinol Metab Clin North Am.* 2012 March; 41(1): 105-117, which is hereby incorporated in its entirety by reference, and discusses research in the field of therapeutic devices for type 1 diabetes to improve glucose monitoring and insulin delivery devices, closed-loop insulin delivery systems, and coupling subcutaneous continuous glucose monitoring and subcutaneous insulin pump delivery to deliver insulin in continually glucose-responsive fashion using a control algorithm to direct insulin delivery according to real-time sensor glucose levels.

Liquid medicaments suitable for delivery to a patient by devices and methods of the invention, including by embodiments of devices and methods discussed herein, include bolus insulins, basal insulins, and amylin agonists, for example. As described herein amylin agonists include amylins, e.g., a human or rodent amylin, and amylin analogues, e.g., pramlintide.

In one aspect, the invention includes a programmable multiple drug chamber medical infusion pump or infusion pump system including a pumping mechanism and a processor, wherein (a) the processor is programmed to calculate a basal amount and delivery rate for delivery of an amylin receptor agonist based on a predetermined basal dosing ratio of the amylin receptor agonist to basal insulin, or range or ratios, wherein the amount and delivery rate are automatically adjusted based on the amount of insulin selected by the user for administration, (b) the processor is programmed to calculate a bolus delivery rate for an amylin receptor agonist based on a predetermined bolus dosing ratio of amylin receptor agonist to bolus insulin, wherein the amount and delivery rate are automatically adjusted based on the amount of insulin selected by the user for administration, and (c) the processor uses these calculations to cause the pumping mechanism to deliver the amylin receptor agonist in dosing amounts and at delivery rates substantially equal to the calculated basal and bolus amounts and rates over programmed periods of time.

In another aspect, the invention includes a programmable medical infusion pump or infusion pump system having a data input device, said pump comprising an amylin agonist drug reservoir, an insulin drug reservoir, one or more pump mechanisms, and a processor in data communication with a data input device and arranged to control the pump mechanism(s), wherein the processor is programmed (a) to deliver a basal insulin amount from the insulin drug reservoir, (b) to deliver an amylin agonist from the amylin agonist drug reservoir at a basal rate to a user by prompting the user to select a basal insulin infusion rate or by referencing a preselected basal insulin infusion rate, (c) calculating an amount and delivery rate for the amylin agonist based on a predetermined ratio of basal amylin agonist to the basal insulin over a predetermined period of time, and (d) to control a pump mechanism to deliver the amylin agonist from the drug reservoir at a delivery rate substantially equal to the calculated basal rate during the period of time.

In one embodiment, the data input device is a keypad or touchscreen or other user interface, for example. In another embodiment the data input device is a smart phone. In another embodiment the data input device is a keypad or touchscreen or other user interface that also works in conjunction with a smart phone, e.g., via a Bluetooth® connection. Herein, a "smart phone" or "smartphone" refers to a mobile phone that is also a computer small enough to fit into a user's hand. They have an advanced mobile operating system (e.g., Android, iOS, Windows Phone, Blackberry, Firefox OS, Sailfish OS, Tizen, Ubuntu Touch, etc.), which combines features of desktop or "personal" computer operating systems with one or more other features useful for mobile or handheld use, e.g., a touchscreen, cell phone, Bluetooth, Wi-Fi, GPS mobile navigation, camera, video camera, speech recognition, voice recorder, music player, near field communication, an infrared reader, accelerometer, thermometer, altimeter, compass, barometer, calculator, etc. Typically, conventional smart phones have two mobile operating systems, a primary, main user-facing software platform that is supplemented by a secondary, low-level proprietary real-time operating system that operates the transceiver and other hardware. Today, most smartphones are able to run multiple one programs or applications, called "apps", at the same time, which helps the user do things more quickly and easily. Examples of smart phones include those in the Apple iPhone family, including the iPhone 4, 4S, 5, 5S, 6, and 6 Plus, Nexus 6 (Google and Motorola), Sony Xperia Z3V, Sony Xperia Z3V Compact, Samsung Galaxy S6, Samsung Galaxy S6 Edge, Samsung Galaxy Note 4, HTC One M9, and LG G3. Other data input devices may be used. Examples of other such devices include smartwatches, personal digital assistants (PDAs), and personal computers. Smartwatches are computerized wristwatches with functionality that is enhanced beyond timekeeping; indeed, smartwatches today are effectively wearable computers. Like smartphones, many smartphones run mobile apps, and some, called "watch phones", feature full mobile phone capability. Examples include the Apple Watch (Apple, Inc.), Sony Smartwatch 3, Gear S (Samsung), Gear Live (Samsung), and G Watch (LG).

In yet another aspect, the invention includes a medical infusion pump or infusion pump system containing a pharmaceutical formulation comprising an amylin agonist and a pharmaceutical formulation comprising an insulin, and the pump is programmed to administer the amylin agonist and the insulin to a subject in an amount and frequency to provide a basal level of the insulin and to provide a basal plasma level of the amylin agonist over a 24-hour period wherein the basal plasma level of the amylin agonist provided over the 24-hour period is equal to from between about 7% to about 15% of the basal level of insulin provided over the same period, and, optionally, programed to administer a mealtime bolus of insulin and to administer a mealtime bolus of an amylin agonist wherein the amylin agonist is administered one or more times per day in an amount and frequency to provide a mealtime bolus of the amylin agonist to the subject that is equal to from between about 2% to about 5% of the mealtime bolus amount of an insulin administered to the subject.

In yet another aspect, the invention includes a programmable medical infusion pump or infusion pump system having a data input device, where the pump comprises an amylin analogue drug reservoir, an insulin drug reservoir, one or more pump mechanisms, and a processor in data communication with a data input device and arranged to control the pump mechanism, and wherein the processor is programmed to (a) deliver a mealtime bolus amount of an insulin from the insulin drug reservoir, (b) to deliver a mealtime bolus amount of an amylin receptor agonist from the amylin receptor agonist drug reservoir to a user by prompting the user to select a mealtime bolus amount of an insulin or by referencing a preselected mealtime insulin bolus amount and infusion rate, (c) calculating an amount and delivery rate for the amylin receptor agonist based on a predetermined ratio of the mealtime amylin receptor agonist bolus to the mealtime insulin bolus over a predetermined period of time, and (d) controlling the pump mechanism to deliver the amylin receptor agonist from the drug reservoir at a delivery rate substantially equal to the calculated mealtime bolus during the period of time.

In yet another aspect, the invention includes a programmable medical infusion pump or infusion pump system having a data input device, where the pump comprises an amylin receptor agonist drug reservoir, an insulin drug reservoir, one or more pump mechanisms, and a processor in data communication with a data input device and arranged to control the pump mechanism, and wherein the processor is programmed to (a) deliver a basal amount of an insulin and a mealtime bolus amount of an insulin to a user from the insulin drug reservoir, (b) to deliver a basal amount of an amylin receptor agonist and a mealtime bolus amount of an amylin receptor agonist from the amylin receptor agonist drug reservoir to a user by prompting the user to select a basal amount of an insulin and a mealtime bolus amount of an insulin, as appropriate or desired, or by referencing a preselected basal amount of an insulin or a mealtime insulin bolus amount and infusion rate, (c) calculating an amount and delivery rate for the amylin receptor agonist based on different predetermined ratios or from different ranges of ratios of a basal amount of an amylin receptor agonist to the basal amount of insulin over a predetermined period of time and a mealtime amylin receptor agonist bolus to the mealtime insulin bolus over a predetermined period of time, and (d) controlling the pump mechanism to deliver the amylin receptor agonist from the drug reservoir at delivery rates substantially equal to the calculated basal amount and mealtime bolus amount(s) during the period(s) of time.

Various ratios may be used to calculate the amounts of an amylin agonist and an insulin to be administered. They include the in vivo molar ratio, the in vivo gram ratio (adjusted for molecular weight), the ex vivo gram ratio (adjusted for bioavailability), and the ex vivo µg/U ratio (for convenience in using insulin). The amounts may be based on area under the curve (AUC) measurements, In another aspect, the amylin agonist provided the medical infusion pump or infusion pump system is pramlintide, and the pump is programmed (a) to administer pramlintide to a subject in an amount and frequency to provide a basal pramlintide level over a 24-hour period that is equal to about 15% of the basal insulin level provided, and (b) to administer a mealtime bolus of pramlintide one or more times per day in an amount and frequency to provide a mealtime bolus of pramlintide to the subject that is equal to about 5% of a mealtime bolus amount of the insulin administered to the subject.

In another aspect, the programmable medical infusion pump or infusion pump system includes a processor that is programmed to calculate a basal amount of an amylin agonist and to deliver the amylin agonist from a drug reservoir at a basal rate by comparing the pharmacokinetics of the amylin agonist and the insulin in order to maintain a basal plasma level of the amylin agonist that is from about 7% to about 15% or from about 5% to about 22% of the basal plasma levels of the insulin, measured on a molar basis. As noted, the basal ratio will be higher than the bolus ratio. In one aspect, the in vivo gram ratio (adjusted for molecular weight) ranges from about 3% to about 15%. In yet another aspect, rather than in vivo molar ratios, the programmable medical infusion pump or infusion pump system includes a processor that is programmed to calculate a basal amount of an amylin agonist and to deliver the amylin agonist from a drug reservoir at a basal rate by comparing the ex vivo gram ratios of the amylin agonist and the insulin in order to provide an amount of the amylin agonist that is from about 6% to about 30% of the amount of the insulin. In yet another aspect, the programmable medical infusion pump or infusion pump system includes a processor that is programmed to calculate a basal amount of an amylin agonist and to deliver the amylin agonist from a drug reservoir at a basal rate by comparing the ex vivo µg/U ratio (for convenience in using insulin) of the amylin agonist and the insulin in order to provide a basal amount of the amylin agonist that is from about 2 micrograms of the amylin agonist to 1 Unit of the basal insulin to about 11 micrograms of the amylin agonist to 1 Unit of the basal insulin. The amylin agonist, in one embodiment, is pramlintide.

In yet another aspect, the programmable medical infusion pump or infusion pump system includes a processor that is programmed to calculate and deliver a bolus amount of an amylin agonist by comparing the pharmacokinetics of the amylin agonist and an insulin in order to deliver a bolus of the amylin agonist to yield a plasma level that is from about 2% to about 5% or from about 2% to about 7% of the plasma level resulting from the bolus administration of the insulin, measured on a molar basis. As noted, the bolus ratio will be lower than the basal ratio. In one aspect, the in vivo gram ratio (adjusted for molecular weight) ranges from about 1% to about 5%. In yet another aspect, rather than in vivo molar ratios, the programmable medical infusion pump or infusion pump system includes a processor that is programmed to calculate and deliver a bolus amount of an amylin agonist from a drug reservoir by comparing the ex vivo gram ratios of the amylin agonist and the insulin in order to provide an amount of the amylin agonist that is from about 2% to about 10% of the amount of the insulin. In yet another aspect, the programmable medical infusion pump or infusion pump system includes a processor that is programmed to calculate a bolus amount of an amylin agonist and to deliver the amylin agonist from a drug reservoir at a bolus rate by comparing the ex vivo µg/U ratio (for convenience in using insulin) of the amylin agonist and the insulin in order to provide a bolus amount of the amylin agonist that is from about 1 microgram of the amylin agonist to 1 Unit of the bolus insulin to about 4 micrograms of the amylin agonist to 1 Unit of the basal insulin. The amylin agonist, in one embodiment, is pramlintide.

In another aspect, the programmable medical infusion pump or infusion pump system includes a processor that is programmed to calculate the basal amount of an amylin agonist to be delivered by further evaluating one or more dosing parameters selected from the group consisting of, for example, mean or median values of amylin agonist/insulin ratios generated from clinical studies, and ranges thereof; subject age; subject body mass index; expected levels of glucagon secretion; subject exercise; and, subject diet.

In another aspect, the invention includes a programmable medical infusion pump or infusion pump system, wherein the processor is programmed to receive data specifying a bolus amount of an amylin agonist and/or an insulin, the duration of administration of the bolus amount(s), the portion of the bolus amount(s) to be delivered immediately upon executing a deliver command and a remainder of the bolus amount(s) to deliver over the duration upon executing a deliver command, thereby controlling the pump mechanism to deliver the bolus.

Figure 9:
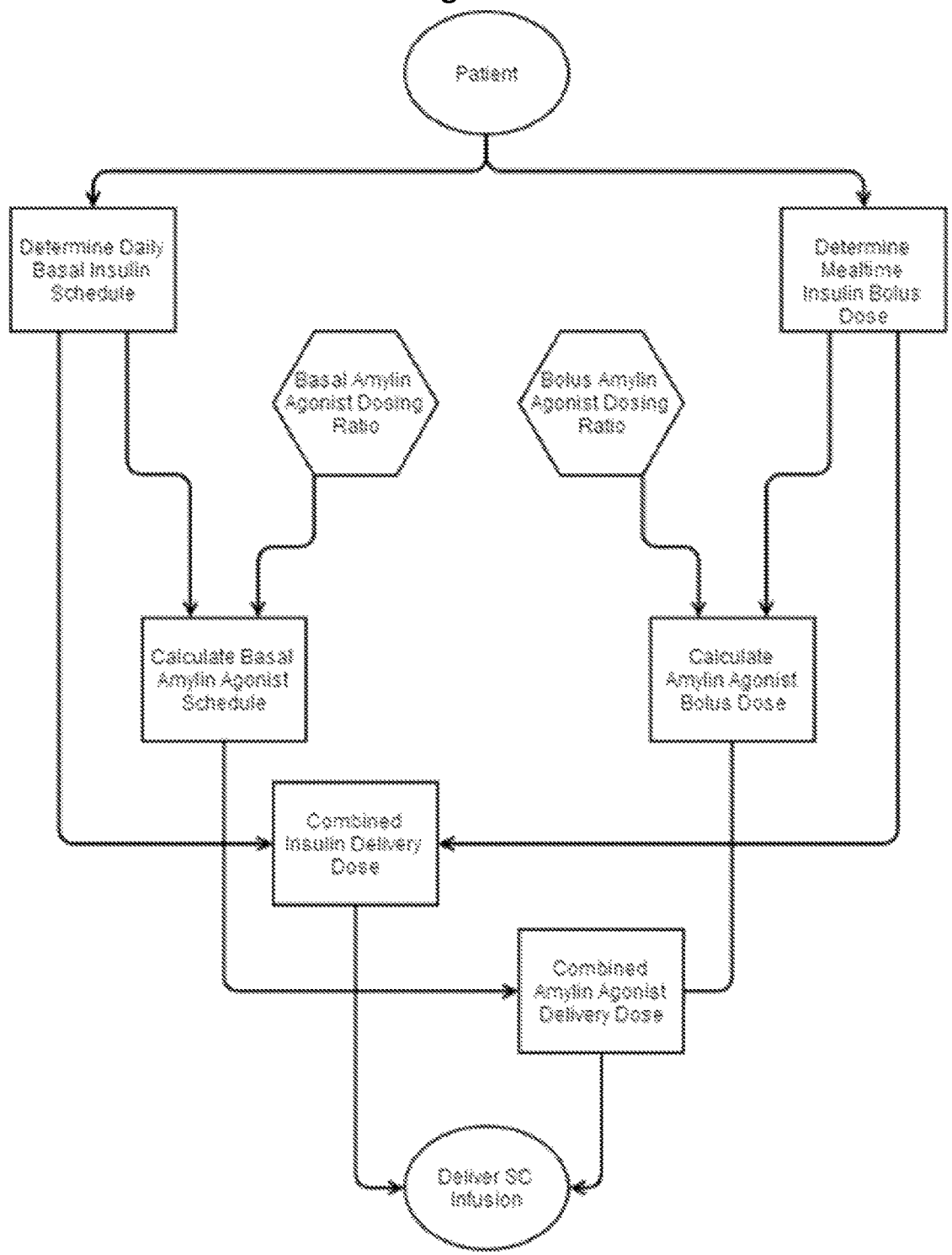
FIG. 9 is a simplified block diagram representation of a programmed implementation of a multiple chamber infusion pump system configured in accordance with selected aspects of the present description.

FIG. 9 is a simplified block diagram representation of an example of a processor-based system that may be included within or coupled to an infusion pump or infusion pump system that may include user devices, including, for example, user interfaces such as touchscreens and/or keypads. The user devices may also be mobile devices such as smartphones, tablets, network-enabled cameras, wearable devices such as Google Glass devices and smart watches.

The FIG. 9 system and one or more of the user devices may be configured in accordance with selected aspects of this document, including the calculation and administration of differential basal/bolus dosing of amylin agonists and insulins based on calculated and/or predetermined dosing ratios, or selected from predetermined ranges or calculated ranges. The FIG. 9 system and/or the one or more user devices may perform the steps of the methods such as the dosing methods described in more detail throughout this document.

FIG. 9 does not show many hardware and software modules, and omits various physical and logical connections. For example, FIG. 9 does not show a pump device or devices, drive mechanisms, housings or infusion cartridges or fluid reservoirs, and other features for delivery of an amylin agonist, preferably in conjunction with an insulin, all of which are known in the art. Also not shown is the user interface, or means for installing or removing a disposable infusion cartridge, for example. Also not shown but includable in the device/system is, for example, a color touch screen, a USB or other connection device or application, and a rechargeable battery.

The FIG. 9 system and the user devices may be implemented as special purpose data processors, general-purpose computers, and groups of networked computers or computer systems configured in accordance with one or more features described in this document. In some embodiments, the FIG. 9 system is built using one or more of, or to include, cloud devices, smart mobile devices, and wearable devices. The FIG. 9 system may also be controlled with a smartphone app.

In one example, referring to FIG. 9, a Patient has decided to use the following basal/bolus regimen for rapid-acting insulin in a pump: Determine Daily Basal Insulin Schedule: 18 Units per day, or 0.75 Units per hour. Determine Mealtime Insulin Bolus Dose: 5 Units three times daily. In this example, the following amylin agonist dosing ratios will be used: Basal Amylin Agonist Dosing Ratio: 5.7 µg/U insulin and Bolus Amylin Agonist Dosing Ratio: 1.9 µg/U insulin. These parameters result in the following amylin agonist doses:

Calculate Basal Amylin Agonist Schedule: 18×5.7=103 µg/day or 4.3 µg/hr.

Calculate Bolus Amylin Agonist Schedule: 5×1.9=9.5 µg three times daily

These calculations would program the separate hormone channels to infuse drug as follows:

Combined Insulin Delivery Dose: 0.75 U/hr plus additional 5 U at each mealtime.

Combined Amylin Agonist Delivery Dose: 4.3 µg/hr plus additional 9.5 µg at each mealtime.

The pump will then Deliver SC Infusion of these amounts (profiles) of drug.

In variants, the FIG. 9 system may function as a server facilitating network-based (e.g., internet-based) or interactions between a user at the infusion pump or infusion pump system or via infusion pump or infusion pump system controller device (e.g., a smart cell phone). The FIG. 9 system may receive real time or stored data flows from a user; each data flow may include dosing information or information relevant to calculating amylin agonist and insulin dosing and dosing ratios, as well as data from other sensors, such as, for example accelerometer data, glucose or other sensor data, and/or audio input. In variants, data is inputted by the user to provide real time information for calculation of amylin agonist and insulin dosing and dosing ratios. In variants, the interaction is facilitated by another system, and the data are provided to the system independent of the infusion pump or infusion pump system or the pump touchscreen or keypad, for example. This may be the case where the data is provided by, for example, a smart phone via a Bluetooth® or other connection. In still other variants, the FIG. 9 system receives and/or implements previously used or inputted data from the user, either in a synchronized manner or with sufficient information to be able to synchronize the amylin agonist and insulin dosing flows; in other words, the FIG. 9 system has sufficient information to correlate the infusion of the different amylin agonist and insulin dosing amounts and flows, so that it "knows" which bolus and which basal dosing flow corresponds to the other bolus and basal dosing flow. Each of the dosing flows is monitored by the FIG. 9 system to provide the proper rate and amount of basal or bolus amylin agonist in comparison to the amount of basal or bolus insulin being administered. Real time blood glucose information may be provided to the FIG. 9 system by a remote blood glucose monitoring system attached to the user and in data connection with the FIG. 9 system.

The simplified block diagram representation in FIG. 9 shows selected processing blocks of a system configured in accordance with selected aspects of the present description. The processing blocks may be implemented with the one or more processor(s) of the system and the infusion pump or infusion pump system device, configured by software stored in one or more storage components. FIG. 9 also does not show many components and connections of the system. The system and process features described herein may be present individually, or in any combination or permutation, except where presence or absence of specific feature(s)/element(s)/limitation(s) is inherently required, explicitly indicated, or otherwise made clear from the context.

Although the process steps and decisions (if decision are required) may be described serially in this document, certain steps and/or decisions may be performed by separate elements in conjunction or in parallel, asynchronously or synchronously, in a pipelined manner, or otherwise. There is no particular requirement that the steps and decisions be performed in the same order in which this description lists them or the Figures show them, except where a specific order is inherently required, explicitly indicated, or is otherwise made clear from the context. Furthermore, not every illustrated step and decision block may be required in every embodiment in accordance with the concepts described in this document, while some steps and decision blocks that have not been specifically illustrated may be desirable or necessary in some embodiments in accordance with the concepts. It should be noted, however, that specific embodiments/variants/examples use the particular order(s) in which the steps and decisions (if applicable) are shown and/or described.

The instructions (machine executable code) corresponding to the method steps of the embodiments, variants, and examples disclosed in this document may be embodied directly in hardware, in software, in firmware, or in combinations thereof. A software module may be stored in non-transitory machine-readable storage medium.

It will be readily apparent to one of ordinary skill in the art that the various devices and processes described herein may be made to include or be implemented by, e.g., appropriately programmed general purpose computers, special purpose computers, and other computing devices, and that the programmable medical infusion pumps or infusion pump systems of the invention also include such a computer or computing device as an integral or separate part of a device or system. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., one or more computer programs, one or more scripts, etc.

The term "compute" means to determine using a processor in accordance with an algorithm encoded, for example, in software.

A "processor" means one or more microprocessors, central processing units (CPUs), computing devices, microcontrollers, digital signal processors, graphics processing units (GPUs), or like devices or any combination thereof, regardless of the architecture (e.g., chip-level multiprocessing or multi-core, RISC, CISC, microprocessor without interlocked pipeline stages, pipelining configuration, simultaneous multithreading, microprocessor with integrated graphics processing unit, GPGPU, etc.).

Thus, a description of a process is likewise a description of an apparatus for performing the process. The apparatus that performs the process can include, e.g., a processor and those input devices and output devices that are appropriate to perform the process. For example, a description of a process is a description of an apparatus comprising a processor and memory that stores a program comprising instructions that, when executed by the processor, direct the processor to perform the method. The apparatus that performs the process can include a plurality of computing devices that work together to perform the process. Some of the computing devices may work together to perform each step of a process, may work on separate steps of a process, may provide underlying services that other computing devices that may facilitate the performance of the process. Such computing devices may act under instruction of a centralized authority. In another embodiment, such computing devices may act without instruction of a centralized authority. Some examples of apparatus that may operate in some or all of these ways may include grid computer systems, cloud computer systems, peer-to-peer computer systems, computer systems configured to provide software as a service, and so on. For example, the apparatus may comprise a computer system that executes the bulk of its processing load on a remote server but outputs display information to and receives user input information from a local user computer.

Further, programs that implement such methods (as well as other types of data) may be stored and transmitted using a variety of media (e.g., computer readable media) in a suitable manner. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

The term "tangible computer-readable medium" refers to a "computer-readable medium" that comprises a hardware component, such as optical or magnetic disks or a solid-state mass storage device. Thus, a description of a process is likewise a description of a computer-readable medium storing a program for performing the process. The computer-readable medium can store (in any appropriate format) those program elements that are appropriate to perform the method. For example, a description of a process is a description of a computer-readable storage medium that stores a program comprising instructions that, when executed by a processor, direct the processor to perform the method. Just as the description of various steps in a process does not indicate that all the described steps are required, embodiments of an apparatus include a computer or computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Various forms of computer readable media may be involved in carrying data (e.g., sequences of instructions, data representing a digital photograph, etc.) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), wireless local area network communication defined by the IEEE 802.11 specifications whether or not they are approved by the WiFi Alliance, SAP, ATP, Bluetooth, and TCP/IP, TDMA, CDMA, and 3G; and/or (iv) encrypted to ensure privacy or prevent fraud in any of a variety of ways well known in the art.

The term "database" refers to any electronically stored collection of data that is stored in a retrievable format.

The term "data structure" refers to a database in a hardware machine such as a computer.

Where databases are used, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device that accesses data in such a database.

The term "network" means a series of points or nodes interconnected by communication paths. For example, a network can include a plurality of computers or communication devices interconnected by one or more wired and/or wireless communication paths. Networks can interconnect with other networks and contain subnetworks.

Various embodiments can be configured to work in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium®, or Centrino, Atom, or Cor. processor, that are adapted to communicate with the computer. Any number and type of devices may be in communication with the computer.

In some embodiments, a server computer or centralized authority may not be necessary or desirable. For example, the present invention may, in an embodiment, be practiced on one or more devices without a central authority. In such an embodiment, any functions described herein as performed by the server computer or data described as stored on the server computer may instead be performed by or stored on one or more such devices.

Where a method or process is described, in an embodiment the process may operate without any user intervention. In another embodiment, the process includes some human intervention (e.g., a step is performed by or with the assistance of a human).

As described above, reference is made in this specification to several embodiments that are schematically illustrated in FIG. 9, which is in a simplified form and omits components and method steps that can be added to the described devices and methods, while including certain optional elements and steps.

In preferred embodiments, a computer-based system is configured as a personal computers or PC, smartphone, tablet, wearable computing device (e.g., Google® Glass) that may operate alone or, preferably, as part of a communication network that includes other computing devices. FIG. 9 does not show hardware and software modules, and omits several physical and logical connections. The system of the invention may be implemented as a special purpose data processor, a general-purpose computer, a computer system, or a group of networked computers or computer systems configured to perform the steps of the methods described in this specification. In some embodiments, the system is built on a personal computer platform, such as a Wintel PC, a Linux computer, or an Apple computer. In other embodiments, the system is built on a mobile telecommunications device platform.

The system includes a processor, read only memory (ROM) module, random access memory (RAM) module, network interface, a mass storage device, and a database coupled together in by a communications bus. The processor may be a microprocessor, and the mass storage device may be a magnetic disk drive, solid-state storage device, or any other suitable electronic data mass storage device. The mass storage device and each of the memory modules—and are connected to the processor to allow the processor to write data into and read data from the system's storage and memory devices. The network interface couples the processor to a network, for example, the Internet and/or a personal or local area network. The nature of the network and of the devices that may be interposed between the system and the network determine the kind of network interface used in the system. In some embodiments, for example, the network interface is an Ethernet interface that connects the system to a local area network, which, in turn, may connect to the Internet. The network may, therefore, in fact include a collection of networks.

The database may be used for storing and organizing data needed to implement the methods of the invention, including amylin/insulin dosing amounts, times, ratios, etc. The database may be a physically separate system coupled to the processor. In alternative embodiments, the processor and the mass storage device can be configured to perform the functions of the database.

The processor may read and execute program code instructions stored in the ROM module, the RAM module, and/or the storage device, or even on a remote server networked with the processor. Under control of the program code, the processor may configure the system to perform the steps of the methods described in this specification. In addition to the ROM/RAM modules and the storage device, the program code instructions may be stored in other machine-readable storage media, such as additional hard drives, solid-state memories, or other machine-readable storage media and/or devices. The program code can also be transmitted over a transmission medium, for example, over electrical wiring or cabling, through optical fiber, wirelessly, or by any other form of physical transmission. The transmission can take place over a dedicated link between telecommunication devices, or through a wide area or a local area network, such as the Internet, an intranet, an extranet, a cloud computing environment or portion thereof, or any other kind of public or private network. The program code may also be downloaded into the system through the network interface or another network interface.

The methods described in this specification may also be performed in a non-networked environment, or more precisely, without reliance on a network. The methods described in this specification can also be performed by computing devices different from those discussed herein. For example, the methods may be performed on a stand-alone user device, for example, a smartphone, tablet, personal digital assistant (PDA), or any other computing device.

The present invention also includes methods, including a method for treating an insulin-using subject with an amylin agonist, comprising the administration of basal and bolus amylin agonist components which are determined by two different dosing ratios to the insulin basal and bolus components administered by the subject. The invention includes methods and therapeutics for dual administration of an insulin and an amylin in different bolus and basal administration ratios to subjects in need of thereof. Bolus amylin/insulin administration ratios and basal amylin/insulin administration ratios are described herein. Ratios may adjusted, or otherwise calculated or determined, as described or referenced herein.

In another aspect, the invention is directed to a method of administering to humans an amylin agonist in combination with insulin in a fashion that does not cause nausea and achieves maximum glucose control efficacy.

In other embodiments, the invention includes (1) methods of calculating the dose of an amylin agonist to be administered based on two components, whereby a first amylin agonist dose is determined by a patient's basal dosing of insulin and a second amylin agonist dose is determined by a patient's bolus dosing of insulin; (2) methods of treating diabetes and other glucose-handling disorders characterized at least in part by hyperglycemia, using a dual chamber hormone pump programmed to calculate the proper infusion rate of an amylin agonist based on two components, whereby the first portion is determined by a patient's basal infusion rate of insulin and the second portion is determined by a patient's bolus infusions of insulin; (3) formulations combining insulin and an amylin agonist in different ratios based upon whether the formulation is for basal or for bolus dosing, with the basal ratio being higher than the bolus ratio. This embodiment also may be carried out, for example, with patch pumps, as noted above.

In one embodiment of the present invention, for example, an amylin agonist is infused such that on a weight-of-drug basis the basal component is greater than the bolus component of total daily dosing. In another embodiment of the present invention, the sizes of an amylin agonist basal rate and bolus doses to be infused are calculated based on defined ratios to the insulin basal rate and bolus doses. In yet another embodiment of the present invention, an amylin agonist and insulin are infused by a dual or multiple chamber pump, or by patch pumps, which is/are programmed to deliver pre-determined or calculated ratios of insulin and amylin agonist basal rates and mealtime boluses depending upon the individual patient's insulin regimen, as summarized herein.

In one aspect, the methods are for treating an insulin-using subject with an amylin agonist comprising basal and bolus amylin agonist components which are determined by two different dosing ratios to the insulin basal and bolus components, with the basal ratio being higher than the bolus ratio.

In another aspect, a method for treating an insulin-using subject with an amylin agonist is provided that comprises administering an amylin agonist to said subject in an amount and frequency to provide a basal plasma level of said amylin agonist over a 24-hour period in a pre-determined ratio to the basal level of an insulin administered to said subject. The insulin may be a basal or long-acting insulin. The amount of basal amylin agonist administered over said period may be equal to, for example, from between about 7% to about 15% of a basal level of an insulin administered to said subject, or other ratios as described or referenced herein. In one aspect, the amount of amylin agonist administered over said period is about 10% to about 15% of the amount of a basal or long-acting insulin during the period of time. In another aspect, the amount of amylin agonist administered over the 24-hour period is about 15% of the amount of a basal or long-acting insulin during the period. In another aspect, the method further comprises administering an amylin agonist one or more times per day in an amount and frequency to provide a mealtime bolus of said amylin agonist in a pre-determined ratio to the bolus amount of an insulin administered to said subject, wherein the pre-determined ratio to said bolus amount is different from and lower than the pre-determined ratio of a basal amount of an amylin agonist to the basal amount of an insulin administered to said subject. In one aspect, the pre-determined ratio of the amount of said amylin agonist provided as a bolus to the amount of an insulin administered as a bolus to said subject is equal to from between about 2% to about 5% or from about 2% to about 7% of a mealtime bolus amount of an insulin administered to said subject, or other ratios as described or referenced herein, including in vivo molar ratios, in vivo gram ratios (adjusted for molecular weight), ex vivo gram ratios (adjusted for bioavailability), and ex vivo µg/U ratios (for convenience in using insulin).

In another aspect, a method for treating an insulin-using subject with an amylin agonist is provided that comprises administering an amylin agonist to said subject in an amount and frequency to provide a basal plasma level of said amylin agonist over a 24-hour period in a pre-determined ratio to the basal level of an insulin administered to subject over the same period of time, and where that ratio is different from the ratio of an amylin agonist to an insulin to be administered as a bolus, for example, as a mealtime bolus.

In one aspect, the amylin agonist is an amylin. In another aspect, the amylin agonist is a derivative of an amylin. In another aspect, the amylin agonist is an agonist analog of an amylin, for example, human amylin or rat amylin. In another aspect, the amylin agonist is pramlintide.

In one aspect, the insulin is a basal or long-acting insulin. In another aspect, the insulin is a bolus or short-acting insulin.

In one aspect, the amylin agonist is administered to a subject in conjunction with insulin. In another aspect, the amylin agonist is pramlintide and it is administered with a basal or a long-acting insulin. In another aspect, the amylin agonist is pramlintide and it is administered with a bolus or a short-acting insulin.

In one aspect, the amylin agonist administered to provide a basal level of amylin agonist and the amylin agonist administered as a mealtime bolus of said amylin agonist is pramlintide.

In one aspect, the amylin agonist and/or the insulin is administered to a subject by injection.

In another aspect, the amylin agonist and/or the insulin is administered to a subject by infusion. In yet another aspect, the amylin agonist and/or the insulin is administered to a subject by subcutaneous continuous infusion.

In one aspect, the amylin agonist and/or the insulin is administered to a subject by a medical infusion pump or infusion pump system. In another aspect, the amylin agonist and/or the insulin are administered to a subject by subcutaneous continuous infusion from a programmable medical infusion pump or infusion pump system.

In one aspect, the subject has a glucose-handling disorder. In one aspect the glucose-handling disorder is any disease, condition or disorder that may be treated with insulin and/or an amylin agonist, e.g., an amylin analogue. In one aspect, the glucose-handling disorder is diabetes. In one aspect, the diabetes Type 1 diabetes. In another aspect, the diabetes is Type 2 diabetes.

In another aspect, the invention includes methods for treating a subject for hyperglycemia and/or defective GCR, comprising (a) administering an amylin agonist to the subject in an amount and frequency to provide a basal plasma level of the amylin agonist over a 24-hour period that is equal to, for example, from between about 7% to about 15% of a basal level of an insulin administered to the subject, or some other predetermined or calculated ratio (which may be referred to as a first predetermined ratio), and (b) administering an amylin agonist to the subject one or more times per day in an amount and frequency to provide a mealtime bolus of the amylin agonist that is equal to from between about 2% to about 5% of a mealtime bolus amount of an insulin administered to the subject, or some other predetermined or calculated ratio (which may be referred to as a second predetermined ratio), wherein the first predetermined ratio is higher than and different from the second predetermined ratio. Other basal and bolus amylin agonist/insulin ratios are described or referenced herein, or may be calculated as described herein, for use in the methods of the invention.

In another aspect, the invention includes a commercial package containing a pharmaceutical formulation containing an amylin agonist for parenteral administration to an insulin-using subject, and the package comprises instructions for administering the amylin agonist in an amount and frequency to provide a basal plasma level of said amylin agonist over a 24-hour period that is equal to from between about 7% to about 15% of a basal level of an insulin to be administered to said subject, or in some other predetermined or calculated ratio. In another aspect, the commercial package further comprises instructions for administering an amylin agonist one or more times per day in an amount and frequency to provide a mealtime bolus of the amylin agonist that is equal to from between about 2% to about 5% of a mealtime bolus amount of an insulin to be administered to said subject, or in some other predetermined or calculated ratio. Other basal and bolus amylin agonist/insulin ratios that are described or referenced herein, or may be calculated as described herein, may be included or referenced in the commercial package of the invention.

In another aspect, the amylin agonist included in the commercial package for bolus administration is pramlintide.

In one aspect, the amylin agonist included in the commercial package for basal administration is a long-acting amylin agonist.

In one aspect, the amylin agonist included in the commercial package for basal administration is pramlintide. In a related aspect, the amylin agonist included in the commercial package for basal administration is pramlintide, and the instructions provide that the basal plasma level of pramlintide to be administered over a 24-hour period is equal to about 15% of the basal level of an insulin to be administered to said subject over the 24-hour period, or some other predetermined or calculated amount. In another aspect, the amylin agonist in the commercial package to be administered as a mealtime bolus is pramlintide, and the amount of pramlintide to be administered as a mealtime bolus is equal to about 5% of the amount of an insulin to be administered as a mealtime bolus to said subject, or some other predetermined or calculated amount as described or referenced herein.

In one aspect, the invention includes pharmaceutical compositions for administration to a subject comprising a basal blend of an insulin and an amylin agonist, where the amylin agonist and the insulin are present in a ratio ranging from about 1:14 to about 1:6 or 1:7, or in another predetermined or calculated ratio as described or referenced herein. In one aspect the amylin agonist in the pharmaceutical composition is pramlintide and the insulin is a basal or long-acting insulin. In another aspect the amylin agonist in the pharmaceutical composition is long-acting amylin agonist and the insulin is a basal or long-acting insulin.

In another aspect, the invention includes pharmaceutical compositions for administration to a subject comprising a bolus blend of an insulin and an amylin agonist, where the amylin agonist and the insulin are present in a ratio ranging from about 1:50 to about 1:20, or in another predetermined or calculated ratio as described or referenced herein. In one aspect the amylin agonist in the pharmaceutical composition is pramlintide and the insulin is a bolus or short-acting insulin. In another aspect the amylin agonist in the pharmaceutical composition is short-acting amylin agonist and the insulin is a bolus or short-acting insulin present in ratios described herein, or otherwise calculated as described herein.

In one aspect, the compositions are useful for the treatment of disorders that can be ameliorated by administration of insulin and/or amylin, or their agonists. In another aspect, the inventions include compositions comprising or consisting essentially of each of these compounds in predetermined ratios for basal administration and bolus administration that are different from each other. As noted, in embodiments the ratio of an amylin agonist to an insulin for basal administration is higher than the ratio of an amylin agonist to an insulin for bolus administration.

The invention includes a pharmaceutical composition comprising one or more pharmaceutically acceptable insulin and amylin agents for the treatment of a glucose disorder, e.g., T1D, T2D, etc., and related diseases, disorders and conditions characterized at least in part by insulin and/or amylin deficiency. Thus, the inventions include pharmaceutical compositions in a form suitable for, or adapted to, treatment of a subject for a such diseases, disorders or conditions. In one embodiment, the disease, disorder or condition is associated with dysglycemia. In certain embodiments, the disease, disorder or condition is any form of diabetes. The form of diabetes may, for example, be T1D. In other embodiments, the disease, disorder or condition is T2D, particularly insulin-using T2D.

In one aspect, the pharmaceutical compositions are formulated for intravenous administration, including by infusion or as a bolus. Administration may be, for example, by subcutaneous or intramuscular injection or by means of a pump, for example a pre-programmed or programmable pump.

The amylin agonist and the amylin agonist/insulin pharmaceutical compositions of the invention, and for use in the methods of the invention, may be formulated for cartridges.

Pharmaceutical compositions according to the present invention may be administered parenterally to patients in need of such a treatment. Parenteral administration may be performed by injection, preferably subcutaneous or intramuscular injection by means of a syringe, optionally a pen-like syringe, or mechanical driven injector. Alternatively, parenteral administration can be performed by means of an infusion pump or infusion pump system.

In another aspect, the compositions of the invention comprise an amylin and an insulin in basal ratios as provided herein, an amylin and an insulin in bolus ratios as provided herein, or in basal or bolus ratios calculated based on the discoveries and description herein. These compositions and amounts may be provided as single or multiple doses.

In one embodiment, the amylin agonist is administered in a single dose. In another embodiment, the amylin agonist is administered in more than one dose. In yet another embodiment, the amylin agonist is administered continuously over a period of time, for example a predetermined period of time. In still another embodiment, insulin or an agonist or analog thereof is co-administered with the amylin agonist.

In another aspect, the treated subject is a mammal, preferably a human. Other mammals include domestic and farm animals, and zoo, sports, or pet animals, such as dogs, horses, and cats.

The inventions include a combined fluid injection and control system and includes a fluid delivery system including at least one pumping device, a fluid path, and a control unit. The fluid path is adapted to connect the pumping device to a patient via a catheter inserted in the patient. The control unit is operable to control the fluid delivery system. In operation, the control unit selectively actuates the fluid delivery system to operate in a fluid injection mode. In the fluid injection mode the pumping device delivers fluid to the fluid path for a fluid injection procedure. An operator control may be connected to the control unit for controlling the fluid delivery system and may be a handheld device.

It will be understood that the inventions include pumps programed to deliver an amount of an amylin agonist in a predetermined or calculated ratio to an amount of a bolus or short-acting insulin and/or a basal or long-acting insulin.

It will be understood that the devices, compositions and methods of the invention for the treatment of a glucose disorder, or any other diseases, disorders and conditions involving treatment with an insulin and an amylin are disclosed.

Treatment of a subject as provided herein with one or more compounds or pharmaceutical compositions as described herein may comprise their simultaneous, separate, sequential or sustained administration.

Pharmaceutical compositions useful for preventing and/or treating a glucose-handling disorder, e.g., diabetes, hyperglycemia, and related diseases, disorders and conditions involving treatment with insulin and/or amylin, are also provided in the form of a combined preparation, for example, as an admixture of two or more amylin agonists with or without an insulin.

The term "a combined preparation" includes not only physical combinations of compounds, but compounds provided as a "kit of parts" in the sense that the combination partners as defined above can be dosed independently or by use of different fixed combinations with distinguished amounts of the combination partners (a) and (b), i.e. simultaneously, separately or sequentially. The parts of the kit can then, for example, be administered simultaneously or chronologically staggered, that is at different time points and with equal or different time intervals for any part of the kit of parts.

In one embodiment, the inventions include a kit comprising one or more doses of an amylin agonist, e.g. an amylin analogue (such as pramlintide) the kit comprising one or more of a syringe, a "pen" injector that delivers a metered dose, a needle-less injector, a liquid formulation, a lyophilized powder and a sterile liquid for reconstitution. In one embodiment a combined preparation is administered, wherein two or more separate compositions are administered to a subject, wherein the first composition comprises a therapeutically effective amount of an amylin, e.g., an amylin agonist, and the second composition comprises a therapeutically effective amount of an insulin.

Methods of the invention include the sequential or simultaneous administration a an amylin agonist, and an insulin as described herein, wherein the bolus insulin is administered in amounts or doses that are less that those used when the bolus insulin are administered alone, i.e., when it not administered together or in combination with an amylin agonist. Such lesser amounts of bolus insulin administered is typically from about 5-25% less, for example, than the amount or amounts of bolus insulin when administered without an amylin agonist.

In another aspect, the invention includes an article of manufacture comprising a vessel containing a therapeutically effective amount of an amylin agonist(s), such as, for example, pramlintide, and instructions for use, including use for the treatment of a subject as described herein. The invention includes an article of manufacture comprising packaging material containing one or more dosage forms as described herein, wherein the packaging material has a label that indicates that the dosage form can be used for a subject having or suspected of having or predisposed to any of the diseases, disorders and/or conditions described or referenced herein, including T1D and T2D, hyperglycemias, and defective GCR.

The invention includes method of preparing a medicament for preventing and/or treating a glucose-handling disorder as described herein, e.g., diabetes or hyperglycemia, comprising bringing together and an amount of an amylin agonist, and a pharmaceutically acceptable carrier together with one or more insulins useful for a glucose-handling disorder as described herein, e.g., diabetes or hyperglycemia.

The invention includes methods for the use of a therapeutically effective amount of an amylin agonist, in the manufacture of a dosage form useful for preventing and/or treating a glucose-handling disorder as described herein, e.g., diabetes or hyperglycemia. Such dosage forms include, for example, parenteral delivery forms and formulations, well as other forms of delivery including forms for delivery by infusion, injection and instillation, and related compositions and devices, for example. Such dosage forms include those for the treatment of a subject as disclosed herein.

In certain other aspect, the invention provides a package comprising an amylin agonist, together with instructions for use in combination with one or more insulins for preventing and/or treating a glucose-handling disorder as described herein, e.g., diabetes or hyperglycemia.

In other aspects, the inventions provide for use of one or more of the compounds and compositions described herein in the manufacture of a medicament. In other aspects, the inventions provide for use of one or more of the compounds and compositions described herein in the manufacture of a medicament for use in the treatment of one or more of the diseases, disorders and conditions described herein.

In other aspects, the invention provides for use of one or more of the compounds, compositions and medicaments described and claimed herein in the treatment of a subject for one or more of the diseases, disorders and conditions described herein.

This document describes in detail the inventive apparatus, methods, and articles of manufacture for estimating quality of interaction. This was done for illustration purposes. The specific embodiments/variants/examples or their features do not necessarily limit the general principles underlying the disclosure of this document. The specific features described herein may be used in some embodiments/variants/examples, but not in others, without departure from the spirit and scope of the invention(s) as set forth herein. Various physical arrangements of components and various step sequences also fall within the intended scope of the disclosure. Many additional modifications are intended in the foregoing disclosure, and it will be appreciated by those of ordinary skill in the pertinent art that in some instances some features will be employed in the absence of a corresponding use of other features. The illustrative examples therefore do not necessarily define the metes and bounds of the invention(s) and the legal protection afforded the invention(s), which are in the claims hereto.

The following sections I-III provide a guide to interpreting this specification.

I. Additional Terms

The terms "an embodiment", "embodiment", "embodiments", "the embodiment", "the embodiments", "one or more embodiments", "some embodiments", "certain embodiments", "one embodiment", "another embodiment" and the like mean one or more (but not all) embodiments of the invention. A reference to "another embodiment" in describing an embodiment does not imply that the referenced embodiment is mutually exclusive with another embodiment (e.g., an embodiment described before the referenced embodiment), unless expressly specified otherwise. Similarly, the mere fact that two (or more) embodiments are referenced does not imply that those embodiments are mutually exclusive. One embodiment of the invention may include or cover or embrace more than one other embodiment of the invention. For example, a first embodiment comprising elements a, b, and c may cover a second embodiment that comprises elements a, b, c, and d as well as a third embodiment covering elements a, b, c, and e. Similarly, each of the first, second, and third embodiments may cover a fourth embodiment comprising elements a, b, c, d, and e.

The terms "including", "comprising", and variations thereof mean "including, but not necessarily limited to". Thus, for example, the sentence "the machine includes a red widget and a blue widget" means the machine includes the red widget and the blue widget, but may possibly include one or more other items as well.

The term "consisting of" and variations thereof mean "including and also limited to". Thus, for example, the sentence "the machine consists of a red widget and a blue widget" means the machine includes the red widget and the blue widget, but does not include anything else.

The phrase "at least one of", when such phrase modifies a plurality of things (such as an enumerated list of things), means any combination of one or more of those things.

Numerical terms such as "one", "two", etc. when used as cardinal numbers to indicate quantity of something (e.g., one widget, two widgets), mean the quantity indicated by that numerical term, but do not mean at least the quantity indicated by that numerical term. For example, the phrase "one widget" does not mean "at least one widget", and therefore the phrase "one widget" does not cover, e.g., two widgets.

The phrase "based on" does not mean "based only on". In other words, the phrase "based on" covers both "based only on" and "based at least on". The phrase "based at least on" is equivalent to the phrase "based at least in part on".

"Herein" means in the present application, including anything that may be incorporated by reference.

"Whereby" is used herein only to precede a clause or other set of words that express only the intended result, objective, or consequence of something that is explicitly recited before the term "whereby".

The term "condition" means (1) a premise upon which the fulfillment of an agreement depends, or (2) something essential to the appearance or occurrence of something else.

The terms "e.g.," "such as", and like terms mean "for example", and thus do not limit the term or phrase they explain. For example, in the sentence "the computer sends data (e.g., instructions, a data structure, etc.) over the Internet", the term "e.g.," explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "i.e.," and like terms mean "that is", and thus limits the term or phrase it explains. For example, in the sentence "the computer sends data (i.e., instructions) over the Internet", the term "i.e.," explains that "instructions" are the "data" that the computer sends over the Internet.

Where two or more terms or phrases are synonymous (e.g., because of an explicit statement that the terms or phrases are synonymous), instances of one such term or phrase does not mean instances of another such term or phrase must have a different meaning. For example, where a statement renders the meaning of "including" to be synonymous with "including but not limited to", the mere usage of the phrase "including but not limited to" does not mean that the term "including" means something other than "including but not limited to".

II. Examples and Terminology are not Limiting

The headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The disclosed invention is widely applicable to numerous embodiments, as is readily apparent from the disclosure. One of ordinary skill in the art will recognize that the disclosed invention may be practiced with various modifications and alterations, such as structural, logical, software, and electrical modifications. Although particular features of the disclosed invention may be described with reference to one or more particular embodiments and/or drawings, it should be understood that such features are not limited to usage in the one or more particular embodiments or drawings with reference to which they are described, unless expressly specified otherwise.

Though an embodiment may be disclosed as including several features, other embodiments of the invention may include fewer than all such features. Thus, for example, a claim may be directed to less than the entire set of features in a disclosed embodiment, and such claim would not be interpreted as requiring features beyond those features that the claim expressly recites.

The present disclosure is not a literal description of all embodiments of the invention. Also, the present disclosure is not a listing of features of the invention that must be present in all embodiments.

All disclosed embodiments are not necessarily covered by the claims (even including all pending, amended, issued and canceled claims). In addition, a disclosed embodiment may be (but need not necessarily be) covered by several claims. Accordingly, where a claim (regardless of whether pending, amended, issued or canceled) is directed to a particular embodiment, such is not evidence that the scope of other claims do not also cover that embodiment.

Devices that are described as in communication with each other need not be in continuous communication with each other, unless expressly specified. On the contrary, such devices need only transmit to each other as necessary or desirable, and may actually refrain from exchanging data most of the time. For example, a machine in communication with another machine via the Internet may not transmit data to the other machine for long period of time (e.g., weeks at a time). In addition, devices that are in communication with each other may communicate directly or indirectly through one or more intermediaries. Devices are in communication with one another if they are capable of at least one-way communication with one another. For example, a first device is in communication with a second device if the first device is capable of transmitting information to the second device. Similarly, the second device is in communication with the first device if the second device is capable of receiving information from the first device.

A description of an embodiment with several components or features does not imply that all or even any of such components or features is required. On the contrary, a variety of optional components are described to illustrate the wide variety of possible embodiments of the present invention. Unless otherwise specified explicitly, no component or feature is essential or required.

Although process steps, algorithms, or the like may be described in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Although a process may be described singly or without reference to other products or methods, in an embodiment the process may interact with other products or methods. For example, such interaction may include linking one business model to another business model. Such interaction may be provided to enhance the flexibility or desirability of the process.

An enumerated list of items (which may or may not be numbered) does not imply that any or all of the items are mutually exclusive, unless expressly specified. Likewise, an enumerated list of items (which may or may not be numbered) does not imply that any or all of the items are comprehensive of any category. For example, the enumerated list "a computer, a laptop, and a tablet computer" does not imply that any or all of the three items of that list are mutually exclusive and does not imply that any or all of the three items of that list are comprehensive of any category.

Also, an enumerated list of items (which may or may not be numbered) does not imply that any or all of the items are equivalent to each other or readily substituted for each other.

All embodiments are illustrative, and do not imply that the invention or any embodiments were made or performed, as the case may be.

III. No disclaimer

Numerous references to a particular embodiment do not indicate a disclaimer or disavowal of additional, different embodiments, and similarly references to the description of embodiments which all include a particular feature do not indicate a disclaimer or disavowal of embodiments which do not include that particular feature. A clear disclaimer or disavowal in the present application will be prefaced by the phrase "does not include" or by the phrase "cannot perform".

What is claimed is:

1. A medical infusion pump system for delivering an insulin and an amylin agonist analog to a patient, said system comprising a user interface, an insulin drug reservoir, an amylin agonist analog drug reservoir, and independent pumping mechanisms for said drug reservoirs, wherein said pumping mechanisms can be regulated by the patient and/or one or more computer algorithms via a processor that (a) sets the basal and bolus rates of insulin infusion to stabilize glucose levels and (b) calculates the basal and bolus rates of amylin agonist analog infusion in ratios to said basal and bolus insulin infusion rates, wherein the amylin agonist analog/insulin basal ratio is different from and higher than the amylin agonist analog/insulin bolus ratio.

2. A medical infusion pump system according to claim 1, wherein said computer algorithm(s) direct said independent pumping mechanisms to provide basal and bolus dosing of said insulin and said amylin agonist analog for stabilization of plasma glucose levels in said patient.

3. A medical infusion pump system according to claim 1, wherein said computer algorithm(s) provide basal and bolus dosing of said insulin and said amylin agonist analog to improve the glucagon counter-regulatory response in said patient.

4. A medical infusion pump system according to claim 1 that is programmable and the molar ratio of basal amylin agonist analog to basal insulin is from about 1:14 to about 1:6 or 1:7; and the ratio of bolus amylin agonist analog to bolus insulin is about 1:50 to about 1:20.

5. A medical infusion pump system according to claim 1, wherein the user interface is a touchscreen, a smart phone, or a smart watch or other wearable device.

6. A medical infusion pump system according to claim 1, wherein the processor is programmed to calculate a basal amount of an amylin agonist analog and to deliver said amylin agonist analog from said drug reservoir at a basal rate by comparing the pharmacokinetics of said amylin agonist analog and said insulin in order to maintain a basal plasma level of said amylin agonist analog that is from about 7% to about 15% or from about 5% to 22% of the basal plasma levels of said insulin.

7. A medical infusion pump system according to claim 1, wherein the processor is programmed to calculate and deliver a bolus amount of an amylin agonist analog by comparing the pharmacokinetics of said amylin analog and said insulin in order to deliver a bolus of said amylin agonist analog to yield a plasma level that is from about 2% to 5% or from about 2% to about 7% of the plasma level resulting from said bolus administration of said insulin.

8. A medical infusion pump system according to claim 1, wherein the processor is programmed to calculate the basal amount of said amylin agonist analog to be delivered by further evaluating one or more dosing parameters selected from the group consisting of mean or median values of amylin agonist analog/insulin ratios generated from clinical studies, and ranges thereof; subject age; subject body mass index; expected levels of glucagon secretion; subject exercise; and, subject diet.

9. A medical infusion pump system according to claim 1, wherein the processor is programmed to receive data specifying a bolus amount, the duration of administration of the bolus amount, the portion of the bolus amount to be delivered immediately upon executing a deliver command and a remainder of the bolus amount to deliver over the duration upon executing a deliver command, and execute the deliver command thereby controlling the drug pump to deliver the bolus.

10. A medical infusion pump system according to claim 1, wherein the amylin agonist analog is pramlintide, and the pump is programmed (a) to administer pramlintide to said subject in an amount and frequency to provide a basal pramlintide level over a 24-hour period that is equal to about 15% of said basal insulin level, and (b) to administer a mealtime bolus of pramlintide one or more times per day in an amount and frequency to provide a mealtime bolus of pramlintide to said subject that is equal to about 5% of a mealtime bolus amount of said insulin administered to said subject.

11. A medical infusion pump system selected from the group consisting of:
(a) a programmable medical infusion pump system having a user interface, said pump comprising a drug reservoir, a drug pump, a data input device, and a processor in data communication with a user interface and arranged to control the drug pump, wherein the processor is programmed to deliver an amylin agonist from said drug reservoir at a differential basal rate and a bolus rate to a user by prompting the user to select a basal or bolus insulin infusion rate or by referencing a preselected basal or bolus insulin infusion rate, calculating a delivery rate for said amylin agonist based on a predetermined ratio of basal or bolus amylin agonist to said basal or bolus insulin over a predetermined period of time, and controlling the drug pump to deliver said amylin agonist from said drug reservoir at a delivery rate according to the calculated basal or bolus rate during the period of time;
(b) a programmable medical infusion pump system having a touchscreen, said pump comprising a drug pump, a data input device, and a processor in data communication with a touchscreen and arranged to control the drug pump, wherein (i) the processor is programmed to deliver an amylin agonist at a basal rate to a user by prompting the user to select a basal insulin infusion rate or by referencing a preselected basal insulin infusion rate, calculating a delivery rate for said amylin agonist based on a predetermined ratio of basal amylin agonist to said basal insulin over a predetermined period of time, (ii) the processor is programmed to deliver a mealtime bolus amount of an amylin agonist to a user by prompting the user to select a mealtime bolus amount of an insulin or by referencing a preselected mealtime insulin bolus amount and infusion rate, calculating a delivery rate for said amylin agonist based on a predetermined ratio of said mealtime amylin agonist bolus to said mealtime insulin bolus over a predetermined period of time, and (iii) the processor controls the drug pump to deliver said amylin agonist in amounts and at delivery rates according to the calculated basal amount and rate and the calculated mealtime bolus amount over said predetermined periods of time;
(c) a programmable medical infusion pump system having a keypad or touchscreen, said pump comprising an amylin agonist drug reservoir, an insulin drug reservoir, one or more drug pumps, a data input device, and a processor in data communication with a keypad or touchscreen and arranged to control the drug pump(s), wherein the processor is programed (i) to deliver a basal insulin amount from said insulin drug reservoir, (ii) to deliver an amylin agonist from said amylin agonist drug reservoir at a basal rate to a user by prompting the user to select a basal insulin infusion rate or by referencing a preselected basal insulin infusion rate, calculating a delivery rate for said amylin agonist based on a predetermined ratio of basal amylin agonist to said basal insulin over a predetermined period of time, and (iii) to control a drug pump to deliver said amylin agonist from said drug reservoir at a delivery rate according to the calculated basal rate during the period of time;
(d) a programmable medical infusion pump system having a keypad or touchscreen, said pump comprising an amylin agonist drug reservoir, an insulin drug reservoir, one or more drug pumps, a data input device, and a processor in data communication with a keypad or touchscreen and arranged to control the drug pump, wherein the processor is programmed to (i) deliver a mealtime bolus amount of an insulin from said insulin drug reservoir, (ii) to deliver a mealtime bolus amount of an amylin agonist from said amylin agonist drug reservoir to a user by prompting the user to select a mealtime bolus amount of an insulin or by referencing a preselected mealtime insulin bolus amount and infusion rate, calculating a delivery rate for said amylin agonist based on a predetermined ratio of said mealtime amylin agonist bolus to said mealtime insulin bolus over a predetermined period of time, and (iii) to control the drug pump to deliver said amylin agonist from said drug reservoir at a delivery rate according to the calculated mealtime bolus during the period of time; and
(e) a medical infusion pump system containing a pharmaceutical formulation comprising an amylin agonist and a pharmaceutical formulation comprising an insulin, said pump being programmed to administer said amylin agonist and said insulin to a subject in an amount and frequency to provide a basal level of said insulin and to provide a basal plasma level of said amylin agonist over a 24-hour period that is equal to from between about 7% to about 15% of said basal level of insulin, and, optionally, programed to administer a mealtime bolus of insulin and to administer a mealtime bolus of an amylin agonist wherein said amylin agonist is administered one or more times per day in an amount and frequency to provide a mealtime bolus of said amylin agonist to said subject that is equal to from between about 2% to about 5% of a mealtime bolus amount of an insulin administered to said subject.

12. A medical infusion pump system according to claim 11, wherein the amylin agonist is pramlintide, and the pump is programmed (a) to administer pramlintide to said subject in an amount and frequency to provide a basal pramlintide level over a 24-hour period that is equal to about 15% of said basal insulin level, and (b) to administer a mealtime bolus of pramlintide one or more times per day in an amount and frequency to provide a mealtime bolus of pramlintide to said subject that is equal to about 5% of a mealtime bolus amount of said insulin administered to said subject.

13. A medical infusion pump system according to claim 11 that is programmable and further comprises at least one of the following:
 (a) the molar ratio of basal amylin agonist to basal insulin is about 1:6 or 1:7;
 (b) the amylin agonist is pramlintide, the insulin is a short-acting insulin, and the ratio of basal pramlintide to basal insulin infusion is from about 1:14 to about 1:6 or 1:7;
 (c) the drug pump is configured to administer said amylin agonist from said drug reservoir by continuous subcutaneous infusion;
 (d) the user interface is a keypad or touchscreen;
 (e) the ratio of bolus amylin agonist to bolus insulin is about 1:20;
 (f) the amylin agonist is pramlintide, the insulin is a long-acting insulin, and the ratio of basal pramlintide to basal insulin infusion is from about 1:50 to about 1:20; and
 (g) the user interface that is a smart phone or smart watch;
 (h) the processor is programmed to calculate a basal amount of an amylin agonist and to deliver said amylin agonist from said drug reservoir at a basal rate by comparing the pharmacokinetics of said amylin agonist and said insulin in order to maintain a basal plasma level of said amylin agonist that is from about 7% to about 15% or from about 5% to 22% of the basal plasma levels of said insulin;
 (i) the processor is programmed to calculate and deliver a bolus amount of an amylin agonist by comparing the pharmacokinetics of said amylin agonist and said insulin in order to deliver a bolus of said amylin agonist to yield a plasma level that is from about 2% to 5% or from about 2% to about 7% of the plasma level resulting from said bolus administration of said insulin;
 (j) the processor is programmed to calculate the basal amount of said amylin agonist to be delivered by further evaluating one or more dosing parameters selected from the group consisting of mean or median values of amylin agonist/insulin ratios generated from clinical studies, and ranges thereof; subject age; subject body mass index; expected levels of glucagon secretion; subject exercise; and, subject diet; and
 (k) the processor is programmed to receive data specifying a bolus amount, the duration of administration of the bolus amount, the portion of the bolus amount to be delivered immediately upon executing a deliver command and a remainder of the bolus amount to deliver over the duration upon executing a deliver command, and execute the deliver command thereby controlling the drug pump to deliver the bolus.

14. A kit comprising a medical infusion pump system according to claim 1 and instructions for administering the amylin agonist analog to the subject one or more times per day in an amount and frequency to provide a mealtime bolus thereof that is equal to from between about 2% to about 5% of the mealtime bolus amount of insulin to be administered to the subject.

15. A kit according to claim 14 wherein medical infusion pump system is programmable and the molar ratio of basal amylin agonist analog to basal insulin is from about 1:14 to about 1:6 or 1:7, and the ratio of bolus amylin agonist analog to bolus insulin is about 1:50 to about 1:20.

16. A medical infusion pump system to deliver an insulin and an amylin agonist analog to a patient, the system comprising:
 (a) a user interface;
 (b) an insulin drug reservoir;
 (c) an amylin agonist analog drug reservoir;
 (d) a processor; and
 (e) at least one pump in fluid communication with the patient and the amylin agonist analog drug reservoir and the insulin drug reservoir, which pump(s) can be controlled by the processor to deliver (a) a basal rate and a bolus rate of insulin infusion to the patient, and (b) a basal rate and a bolus rate of amylin agonist analog infusion to patient, wherein the processor calculates the basal and bolus rates of amylin agonist analog infusion in ratios to the basal and bolus insulin infusion rates, wherein the ratio of basal amylin agonist analog to basal insulin is a molar ratio of from about 1:14 to about 1:6 or 1:7 and the ratio of bolus amylin agonist analog to bolus insulin is a molar ratio of from about 1:50 to about 1:20.

17. A medical infusion pump system according to claim 16 wherein the processor is configured to:
 (a) calculate a basal amount of an amylin agonist analog to deliver to the patient and control the pump to deliver the amylin agonist analog from the amylin agonist analog drug reservoir at a basal rate by comparing the pharmacokinetics of the amylin agonist analog and the insulin in order to maintain a basal plasma level of the amylin agonist analog that is from about 5% to 22% of the basal plasma level of the insulin; and
 (b) calculate a bolus amount of an amylin agonist analog to deliver to the patient and control the pump to deliver the bolus amount of the amylin agonist analog from the amylin agonist analog drug reservoir by comparing the pharmacokinetics of the amylin analog and the insulin in order to deliver a bolus of the amylin agonist analog to yield a plasma level in the patient that is from about 2% to about 7% of the plasma level in the patient that results from delivery of bolus administration of the insulin from the system.

18. A medical infusion pump system according to claim 17 wherein when the amylin agonist analog is pramlintide, the processor is configured to control delivery of the pramlintide to the patient from the system in an amount and frequency (a) to provide a basal pramlintide level over a 24-hour period that is equal to about 15% of the basal insulin level, and (b) a mealtime bolus of pramlintide one or more times per day that is equal to about 5% of a mealtime bolus amount of the insulin administered to the patient.

19. A kit comprising a medical infusion pump system according to claim 16 and instructions for use of the medical infusion pump system to deliver to the (a) a basal rate and a bolus rate of insulin, and (b) a basal rate and a bolus rate of amylin agonist analog such that the basal and bolus delivery of the amylin agonist analog are in ratios to the basal and bolus delivery of insulin, wherein the ratio of basal amylin agonist analog to basal insulin is a molar ratio of from about 1:14 to about 1:6 or 1:7 and the ratio of bolus amylin agonist analog to bolus insulin is a molar ratio of from about 1:50 to about 1:20.

\* \* \* \* \*